(12) United States Patent
DeCosta et al.

(10) Patent No.: US 8,049,023 B2
(45) Date of Patent: Nov. 1, 2011

(54) REAGENTS AND METHODS FOR THE BETA-KETO AMIDE SYNTHESIS OF A SYNTHETIC PRECURSOR TO IMMUNOLOGICAL ADJUVANT E6020

(75) Inventors: Bruce DeCosta, Salem, NH (US); Francis G. Fang, Andover, MA (US); James E. Foy, Andover, MA (US); Lynn Hawkins, Concord, MA (US); Charles Lemelin, North Chelmsford, MA (US); Xiang Niu, Watertown, MA (US); Kuo-Ming Wu, Acton, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/945,959

(22) Filed: Nov. 15, 2010

(65) Prior Publication Data

US 2011/0060151 A1    Mar. 10, 2011

Related U.S. Application Data

(62) Division of application No. 12/338,517, filed on Dec. 18, 2008, now Pat. No. 7,919,643.

(60) Provisional application No. 61/014,648, filed on Dec. 18, 2007.

(51) Int. Cl.
*C07C 229/00* (2006.01)

(52) U.S. Cl. .................................... 554/109
(58) Field of Classification Search .................. 554/109
See application file for complete search history.

(56) References Cited

U.S. PATENT DOCUMENTS

| | | | |
|---|---|---|---|
| 6,290,973 B1 | 9/2001 | Hawkins et al. | |
| 6,521,776 B2 | 2/2003 | Hawkins et al. | |
| 6,551,600 B2 | 4/2003 | Hawkins et al. | |
| 2007/0082875 A1 | 4/2007 | Fang et al. | |

FOREIGN PATENT DOCUMENTS

WO    WO 2007/005583 A1    1/2007

OTHER PUBLICATIONS

Written Opinion of the International Searching Authority for PCT/US2008/087435 dated Oct. 11, 2010.

Morissette et al., Advanced Drug Delivery Reviews 2004, 56, 275-300.
Vippagunta et al., abstract, Vippagunta, Sudha R., "Crystalline Solids.", Advanced Drug Delivery Reviews, 48(2001): 3-26.

*Primary Examiner* — Rebecca Anderson
*Assistant Examiner* — Samantha Shterengarts
(74) *Attorney, Agent, or Firm* — Myers Bigel Sibley & Sajovec, P.A.

(57) ABSTRACT

This invention relates to the synthesis for a precursor of E6020, compound 26, via a β-keto amide alcohol intermediate, compound 22. The synthesis reacts compound 22 with compound 25 and the resultant intermediate is oxidized to produce compound 26, the precursor to E6020. Compounds 22 and 25, and their crystalline forms, represent separate embodiments of the invention. The invention also relates to compounds of formulas (3) and (4) and processes for their preparation.

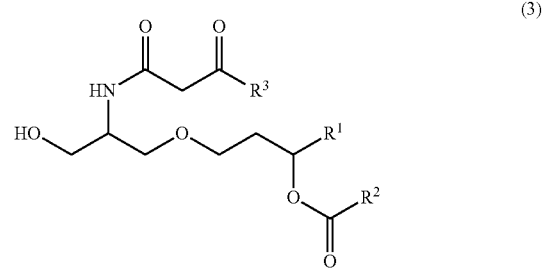

(3)

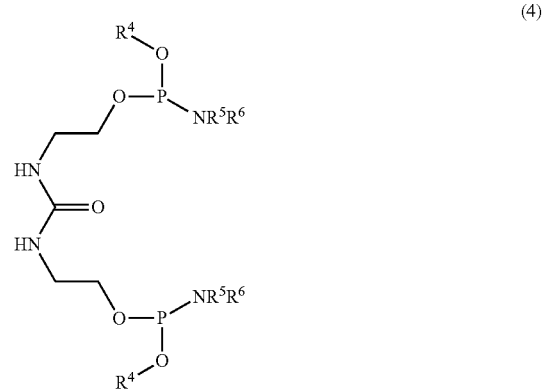

(4)

The β-keto amide alcohol intermediate compound 22 is a compound of formula (3). Compound 25 is a compound of formula (4).

15 Claims, 8 Drawing Sheets

REAGENTS AND METHODS FOR THE BETA-KETO AMIDE SYNTHESIS OF A SYNTHETIC PRECURSOR TO IMMUNOLOGICAL ADJUVANT E6020

CROSS-REFERENCE TO RELATED APPLICATIONS

This application is a divisional application of U.S. application Ser. No. 12/338,517, filed Dec. 18, 2008, which claims priority under 35 U.S.C. §119 to U.S. provisional application Ser. No. 61/014,648 filed Dec. 18, 2007, both of which are incorporated herein by reference.

FIELD OF THE INVENTION

This invention relates to the synthesis of precursors of the immunological adjuvant E6020 via a β-keto amide intermediate. The invention also relates to intermediate compounds in that synthesis and, for two compounds, their crystalline forms.

BACKGROUND OF THE INVENTION

Vaccines have proven to be successful methods for the prevention of infectious diseases. Generally, they are cost effective, and do not induce antibiotic resistance to the target pathogen or affect normal flora present in the host. In many cases, such as when inducing anti-viral immunity, vaccines can prevent a disease for which there are no viable curative or ameliorative treatments available.

Vaccines function by triggering the immune system to mount a response to an agent, or antigen, typically an infectious organism or a portion thereof that is introduced into the body in a non-infectious or non-pathogenic form. Once the immune system has been "primed" or sensitized to the organism, later exposure of the immune system to this organism as an infectious pathogen results in a rapid and robust immune response that destroys the pathogen before it can multiply and infect enough cells in the host organism to cause disease symptoms. The agent, or antigen, used to prime the immune system can be the entire organism in a less infectious state, known as an attenuated organism, or in some cases, components of the organism such as carbohydrates, proteins or peptides representing various structural components of the organism.

In many cases, it is necessary to enhance the immune response to the antigens present in a vaccine in order to stimulate the immune system to a sufficient extent to make a vaccine effective, i.e., to confer immunity. Many protein and most peptide and carbohydrate antigens, administered alone, do not elicit a sufficient antibody response to confer immunity. Such antigens need to be presented to the immune system in such a way that they will be recognized as foreign and will elicit an immune response. To this end, additives (adjuvants) have been devised which stimulate, enhance and/or direct the immune response toward a selected antigen.

The best known adjuvant, Freund's complete adjuvant, consists of a mixture of mycobacteria in an oil/water emulsion. Freund's adjuvant works in two ways: first, by enhancing cell and humoral-mediated immunity, and second, by blocking rapid dispersal of the antigen challenge (the "depot effect"). However, due to frequent toxic physiological and immunological reactions to this material, Freund's adjuvant cannot be used in humans.

Another molecule that has been shown to have immunostimulatory or adjuvant activity is endotoxin, also known as lipopolysaccharide (LPS). LPS stimulates the immune system by triggering an "innate" immune response, a response that has evolved to enable an organism to recognize endotoxin (and the invading bacteria of which it is a component) without the need for the organism to have been previously exposed. While LPS is too toxic to be a viable adjuvant, molecules that are structurally related to endotoxin, such as monophosphoryl lipid A ("MPL") have been tested as adjuvants in clinical trials. Both LPS and MPL have been demonstrated to be agonists to the human toll-like receptor-4 (TLR-4). Currently, however, the only FDA-approved adjuvant for use in humans is the aluminum persulfate salt, Alum, which is used to "depot" antigens by precipitation of the antigens. Alum also stimulates the immune response to antigens.

E6020 is a potent TLR-4 receptor agonist, and thus is useful as an immunological adjuvant when co-administered with antigens such as vaccines for bacterial and viral diseases. For example, E6020 may be used in combination with any suitable antigen or vaccine component, e.g., an antigenic agent selected from the group consisting of antigens from pathogenic and non-pathogenic organisms, viruses, and fungi. As a further example, E6020 may be used in combination with proteins, peptides, antigens and vaccines which are pharmacologically active for disease states and conditions such as smallpox, yellow fever, cancer, distemper, cholera, fowl pox, scarlet fever, diphtheria, tetanus, whooping cough, influenza, rabies, mumps, measles, foot and mouth disease, and poliomyelitis, as well as viral diseases such as herpes and herpes-related diseases and hepatitis and hepatitis-related diseases. When used as a vaccine, E6020 and the antigen are each present in an amount effective to elicit an immune response when administered to a host animal, embryo, or ovum being vaccinated therewith.

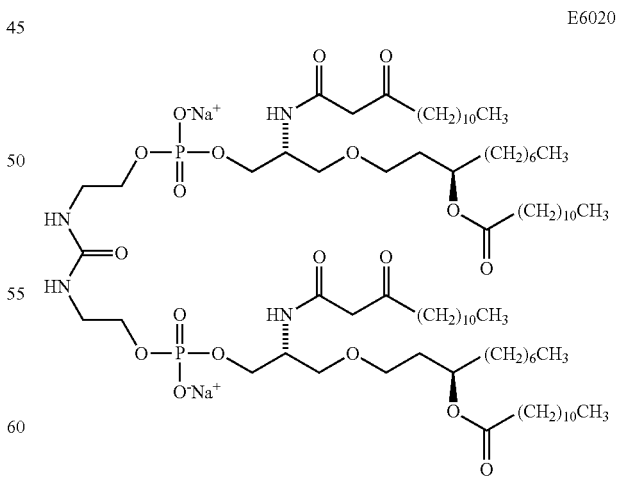

E6020

With their ability to stimulate a more robust antibody response than with an antigen alone, compounds such as E6020 are important immunological compounds. There is a need to develop synthetic methods for preparing compounds such as E6020, and their synthetic precursors, which can be co-administered with antigens in vaccines. New synthetic methods involve new compounds as intermediates and new reactions as method steps. The invention provides an improved method for synthesizing intermediates and precursors for TLR-4 receptor agonists, such as E6020.

SUMMARY OF THE INVENTION

This invention relates to a new synthesis, intermediates and precursors leading to E6020 precursor Compound 26 via a β-keto amide intermediate Compound 22. The synthesis of the invention starts from Compound 14 to prepare Compound 22, which is then reacted with Compound 25 in the preparation of Compound 26, the penultimate precursor to the immunological adjuvant E6020. Compounds 22 and Compound 25, and their crystalline forms, represent separate embodiments of the invention.

In another embodiment, the invention relates to a compound of formula (3):

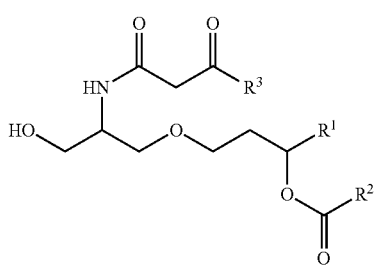

(3)

wherein $R^1$, $R^2$ and $R^3$ are in each occurrence independently a $C_5$-$C_{15}$ alkyl group, a $C_5$-$C_{15}$ alkenyl group, or a $C_5$-$C_{15}$ alkynyl group. The invention also relates to a process for preparing compounds of formula (3). The β-keto amide intermediate Compounds 22 is a compound of formula (3).

Another embodiment of the invention is a compound of formula (4):

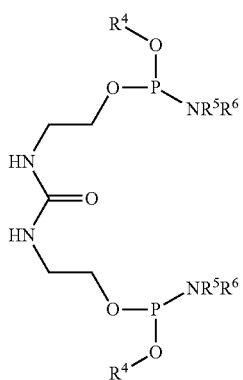

(4)

wherein $R^4$ is in each occurrence independently a protecting group, such as a $C_1$-$C_6$ alkyl group, a $C_3$-$C_5$ alkenyl group, an aryl group, a benzyl group or another suitable protecting group; and each of $R^5$ and $R^6$ is, independently in each occurrence, a $C_1$-$C_6$ alkyl group or, taken together with the nitrogen to which they are attached, form a 5- or 6-membered heterocyclic ring. The invention also relates to a process for preparing compounds of formula (4). Compound 25 is a compound of formula (4).

DETAILED DESCRIPTION OF THE INVENTION

Figure 1:
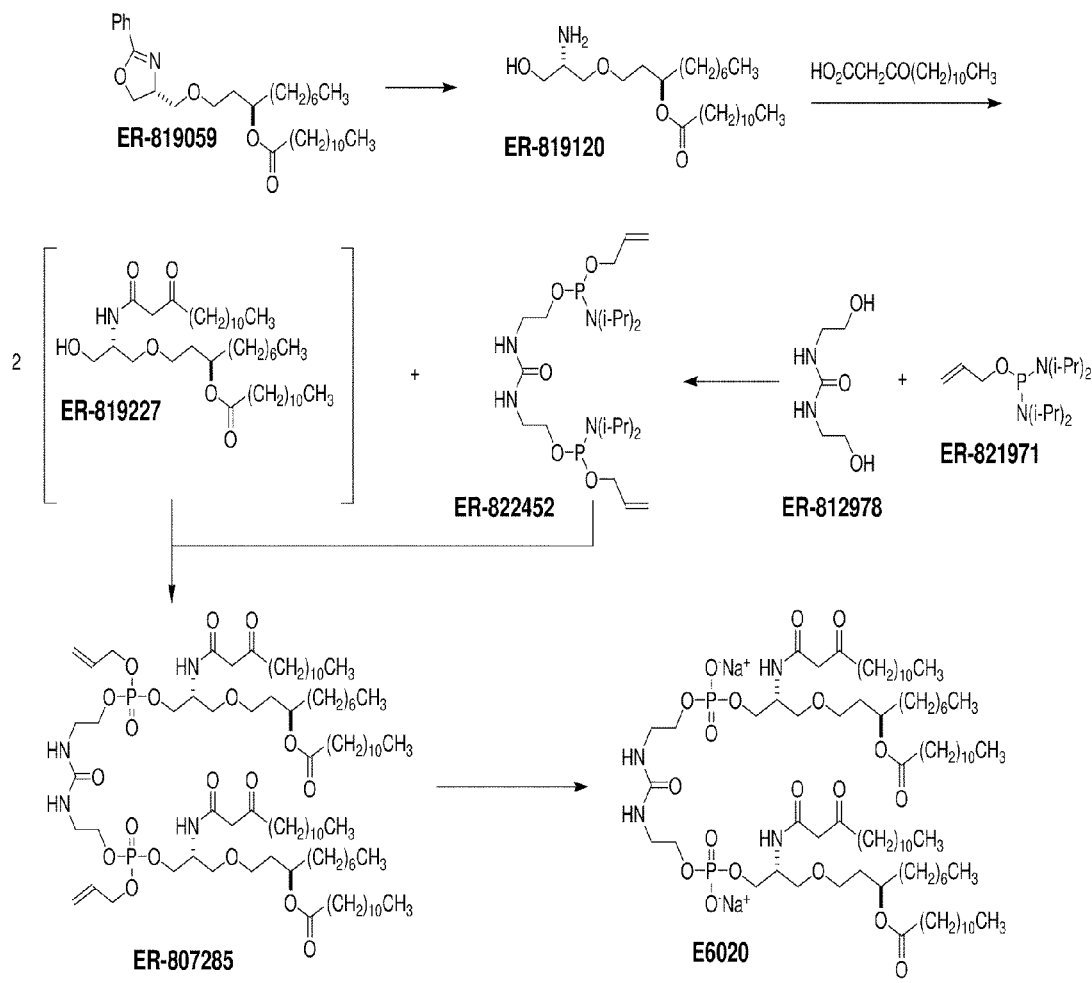
FIG. 1 is an overview of the β-keto amide synthesis of E6020 according to the invention.

U.S. patent application Ser. No. 11/477,936 "Compounds For Preparing Immunological Adjuvant" filed Jun. 30, 2006 (published Apr. 12, 2007 as US 2007-0082875 A1) describes the synthesis of E6020 and is incorporated herein by reference. That synthesis proceeds through a phosphoric acid ester ureido dimer, Compound 19. Schemes 1-3 of US 2007-0082875 A1 depict the synthesis of E6020 via Compound 19. The starting materials shown in Scheme 1 are ER-028694 (1,3-decanediol; commercially available from vendor Mitsui & Co. (US), New York, N.Y.; manufacturer Nippon Fine Chemicals) and ER-807277 (4-Oxazolemethanol, 4,5-dihydro-2-phenyl-, (4R)-propanediol; commercially available from Catalytica Pharmaceuticals, Boonton, N.J.). The penultimate precursor to E6020 is Compound 26.

This invention relates to a new synthesis, intermediates and precursors leading to E6020 precursor Compound 26 via a β-keto amide intermediate Compound 22. The synthesis of the invention starts from Compound 14 to prepare Compound 22, which is then reacted with Compound 25 in the preparation of Compound 26, the precursor to the immunological adjuvant E6020. These steps of the synthesis of the invention, the preparation of the β-keto amide intermediate (3) followed by a condensation of the β-keto amide (3) with a urea diphosphoramidite (4), are shown in Scheme 4 and described below in detail. Compounds 22 and 25, and their crystalline forms, represent separate embodiments of the invention.

Obtaining a crystalline form of a compound, such as Compound 22 or 25, is extremely useful in drug development. Solid state forms (crystalline or amorphous) of a compound can have different physical and chemical properties, for example, solubility, stability, or the ability to be reproduced. These properties often permit the optimization of manufacturing processes, particularly where a crystalline intermediate is obtained. In multi-step syntheses, such as those described herein, intermediates are prepared and unwanted by-products or impurities can be carried forward from earlier steps. Often filtration, separation, and/or purification steps are introduced to remove unwanted by-products or impurities. Introducing such steps not only can increase manufacturing costs but can also decrease the overall yield of the synthesis. Having a crystalline intermediate within a multi-step synthesis can address these problems. A crystalline intermediate provides certain advantages—a high purity intermediate can reduce the need for other purification steps and reduce the cost of the synthetic process.

Scheme 1
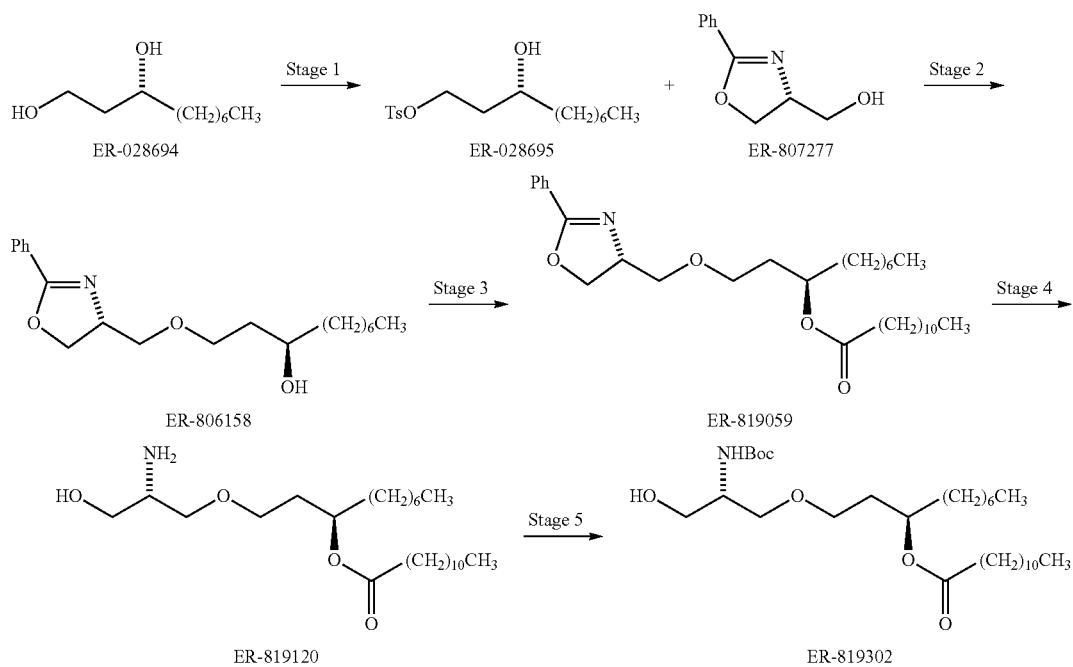
Stage 1: TsCl, Et₃N, THF.
Stage 2: NaHMDS, THF, chromatography, crystallization.
Stage 3: Lauric acid, EDC, DMAP, CH₂Cl₂, chromatography.
Stage 4: H₂, 10% Pd/C, EtOH.
Stage 5: Boc₂O, THF, chromatography.
Scheme 2
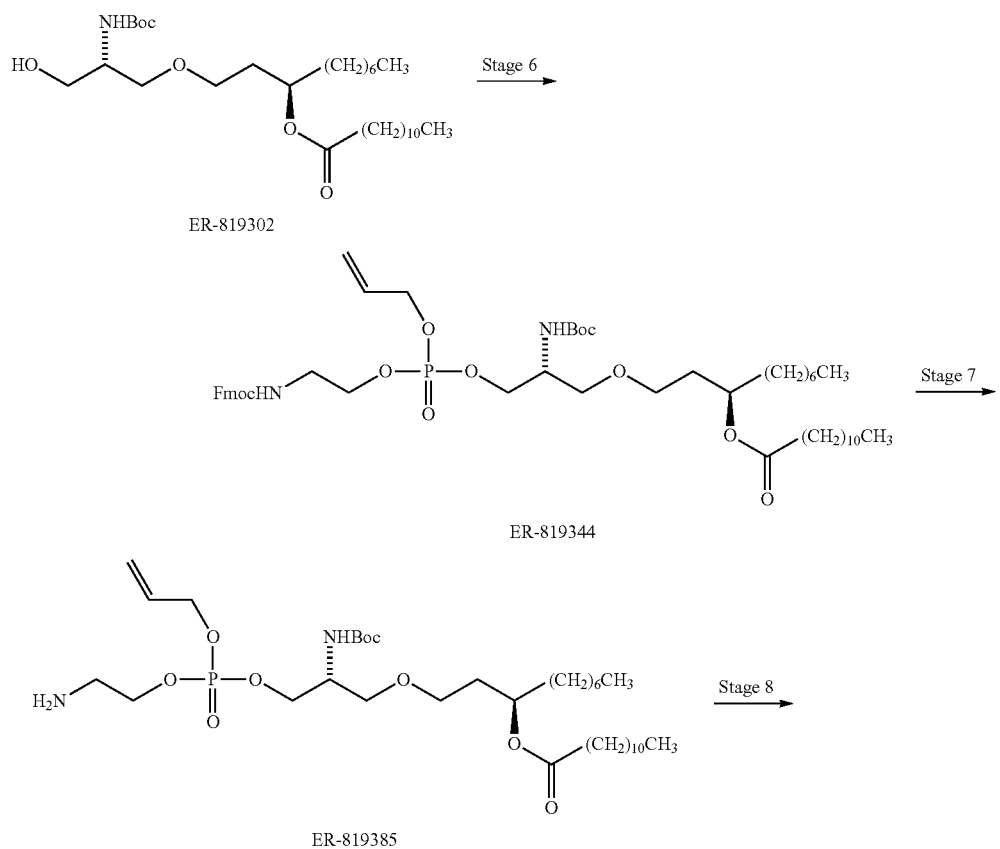

-continued
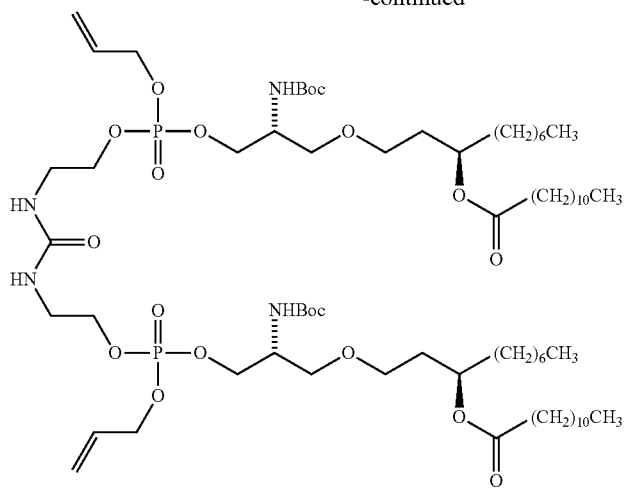
ER-819409
Stage 6: a. Diisopropylamine, Py•TFA, ((iPr)₂N)₂P(OAllyl), CH₂Cl₂
b. HOAc, Py•TFA, FmocNH(CH₂)₂OH
c. H₂O₂, chromatography
Stage 7: Dimethylamine, THF.
Stage 8: 20% Phosgene in Toluene, saturated aqueous NaHCO₃, chromatography
Scheme 3
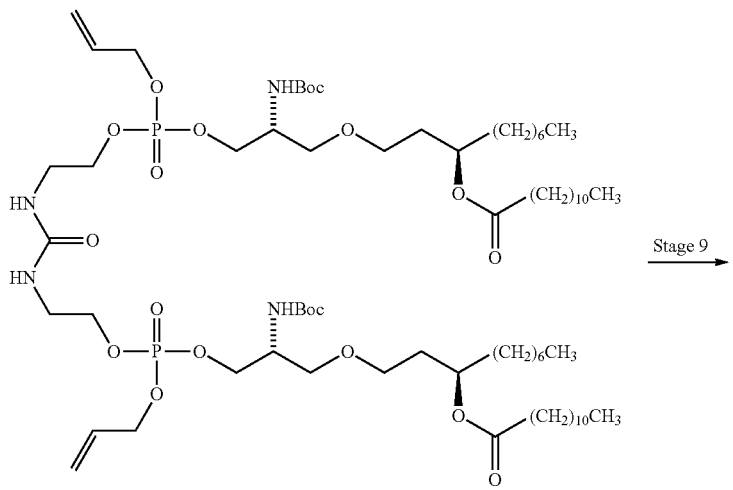
ER-819409
Stage 9 →
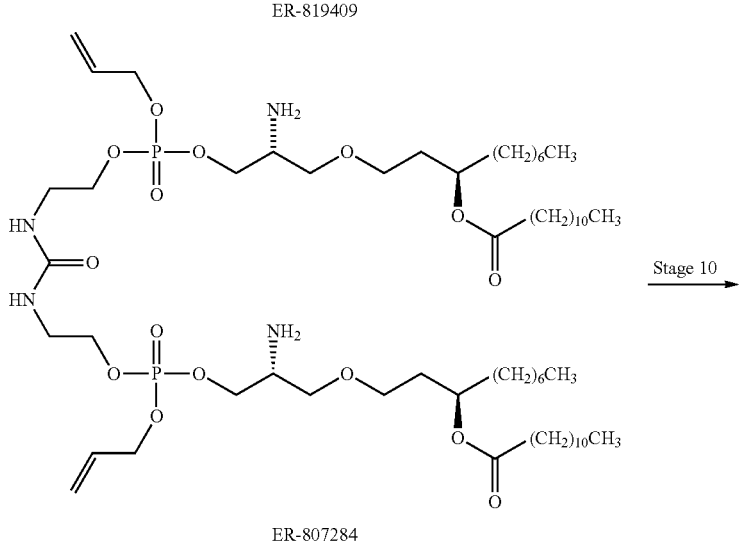
ER-807284
Stage 10 →

-continued
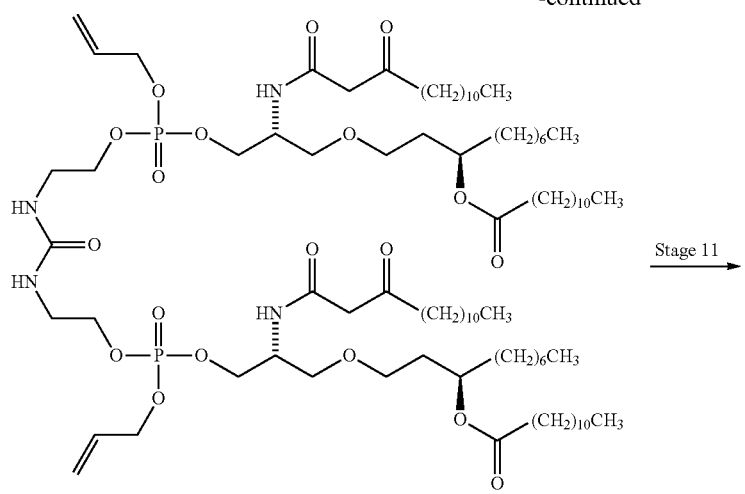
ER-807285
Stage 11
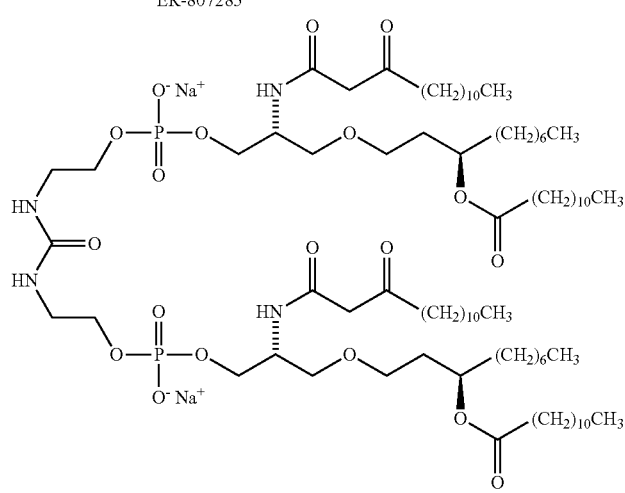
E6020
Stage 9: TFA, CH$_2$Cl$_2$.
Stage 10: 3-Oxo-tetradecanoic acid, EDC, DMF, chromatography.
Stage 11: Pd(PPh$_3$)$_4$, PPh$_3$, PhSiH$_3$, THF, chromatography.
Scheme 4
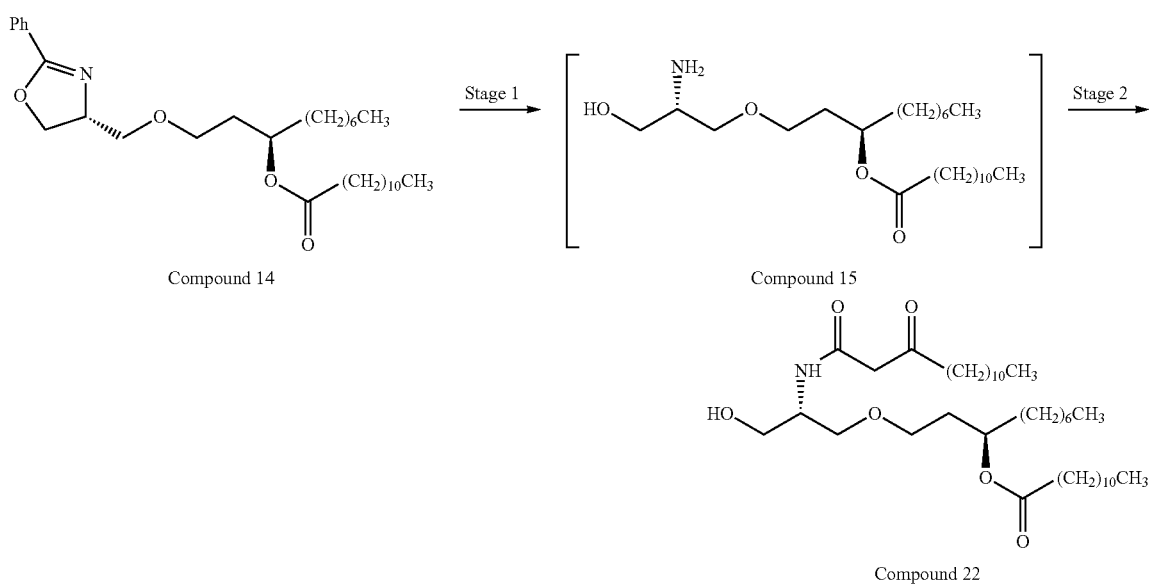

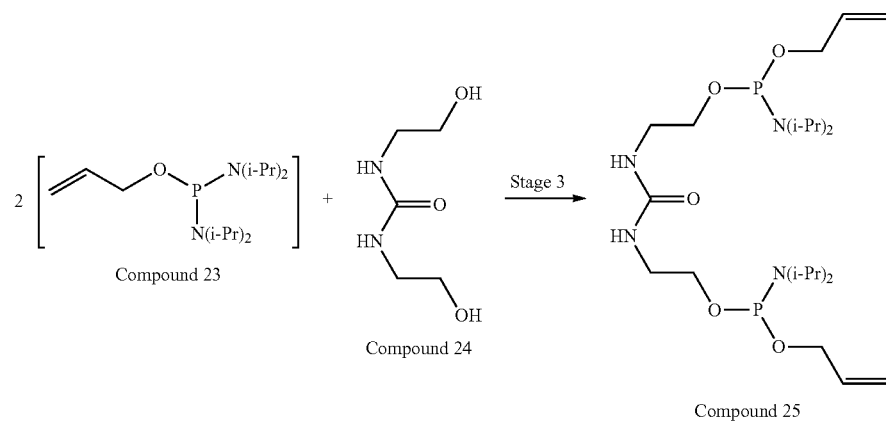
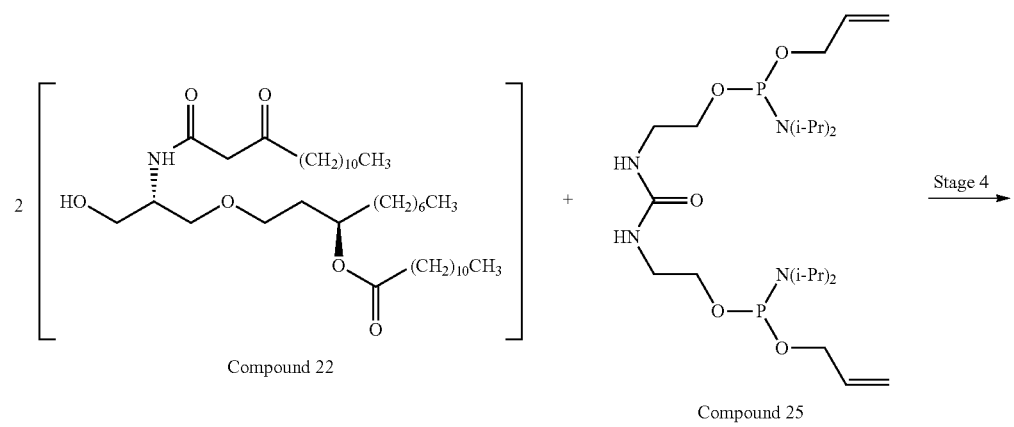
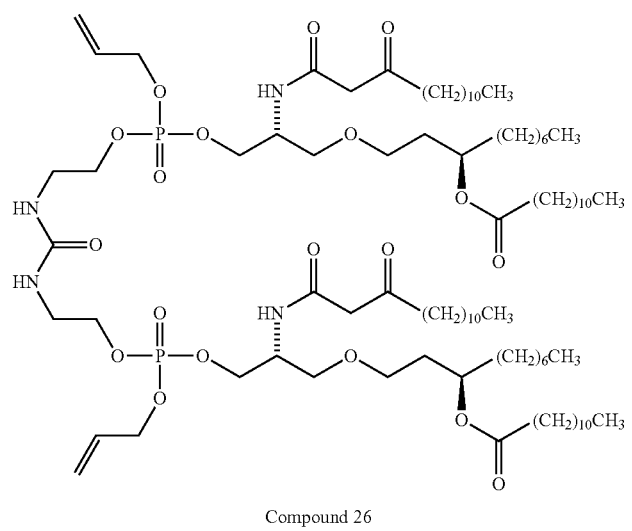
Stage 1: H₂, Pd/C, IPA
Stage 2: 3-Oxo-tetradecanoic acid, CDI, ACN, crystallization
Stage 3: Py•TFA, ACN, crystallization
Stage 4: ACN, heptane, HOAc, H₂O₂, Na₂S₂O₃, chromatography Preparation of the β-Keto Amide Alcohol Intermediate (3).

The synthesis of Compound 26, and similar compounds, first involves reaction of an α-hydroxyl amine of formula (1) with a compound of formula (2) to form a β-keto amide of formula (3) under suitable reaction conditions. This is shown in Scheme 5.

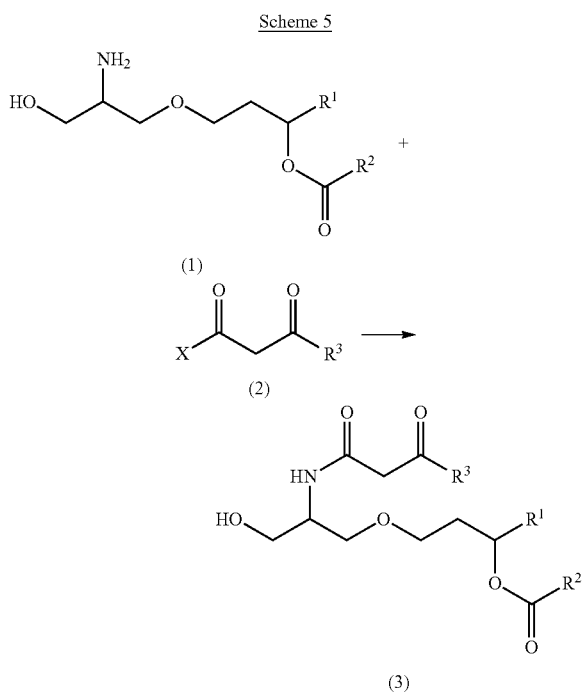

Preparing compound (3) according to Scheme 5 may be achieved using different preparations. The groups $R^1$, $R^2$ and $R^3$ are as defined below. Because $R^1$, $R^2$ and $R^3$ may vary independently one from the other, compound (3) may have symmetrical or asymmetrical groups at $R^1$, $R^2$ and $R^3$. In compound (2), X is a suitable leaving group such as, for example, OH, Cl, F, an imidazolidyl, a carbonate, and an ester. Preferred leaving groups include OH, Cl, F, imidazolidyl, trimethyl acetoxy, ethyl carbonate, methyl carbonate, isobutyl carbonate or a group of the formula Z:

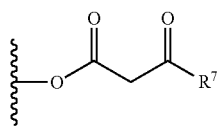

where $R^7$ and $R^3$ in formula (2) are identical such that the compound of formula (2) is a symmetrical beta ketoester anhydride. Such anhydrides can be obtained from the condensation of two identical beta-ketoacid molecules.

In one preparation, compound (3) could be obtained from the condensation of compound (1) with compound (2) where X is imidazolide. The latter is obtained from the activation of compound (2) where X is OH (carboxylic acid) with CDI, (carbonyldiimidazole), reagent in a polar aprotic solvent such as acetonitrile.

In a second preparation, compound (3) could also be obtained from the condensation of compound (1) with compound (2) where X is OH (carboxylic acid) in the presence of an amide bond coupling reagent like HBTU, (O-(benzotriazol-1-yl)-N,N,N',N'-tetramethyluronium hexafluorophosphate), or other coupling reagents in the same family and a tertiary amine base (e.g. Hünig's base, N,N-diisopropylethylamine) in a solvent such as DMF or $CH_2Cl_2$. In addition carbodiimide reagents such as EDC (N-(3-dimethylaminopropyl)-N-ethyl carbodiimide hydrochloride), can be used to activate compound (2) where X is OH (carboxylic acid).

A third preparation to prepare compound (3) is the condensation of compound (1) with compound (2) where X is F (acyl fluoride) in the presence of a tertiary amine base (e.g. Hünig's base) in a solvent like $CH_2Cl_2$. Compound (2) where X is F (acyl fluoride) can be generated from the activation of compound (2) where X is OH (carboxylic acid) with TFFH, (fluoro-N,N,N',N'-tetramethylformamidinium hexafluorophosphate), reagent in a solvent such as $CH_2Cl_2$.

Compound (3) could also be obtained via a fourth preparation from the condensation of compound (1) with compound (2) where X is Cl (acyl chloride) in the presence of a tertiary amine base (e.g. Hünig's base) in a solvent such as $CH_2Cl_2$. Compound (2) when X is Cl (acyl chloride) can be generated from the activation of compound (2) where X is OH (carboxylic acid) with oxalyl chloride reagent in a solvent such as $CH_2Cl_2$.

A fifth preparation can prepare compound (3) from the condensation of compound (1) with alkanoic acid carbonic acid anhydride compound (2) where X is a carbonate in the presence of a tertiary amine base (e.g. Hünig's base) in a solvent such as $CH_2Cl_2$. The latter is obtained from the activation of (2) where X is OH (carboxylic acid) with ethyl chloroformate reagent in the presence of a tertiary amine base (e.g. triethylamine) in a solvent such as $CH_2Cl_2$.

A sixth preparation can prepare compound (3) from the condensation of compound (1) with mixed anhydride compound (2) where X is an ester in the presence of a tertiary amine base (e.g. Hünig's base) in a solvent such as $CH_2Cl_2$. The latter is obtained from the activation of (2) where X is OH (carboxylic acid) with pivaloyl chloride reagent in the presence of a tertiary amine base (e.g. triethylamine) in a solvent such as $CH_2Cl_2$.

Compound (3) could also be obtained via a seventh preparation where compound (2) X is OH (carboxylic acid) is first converted into a symmetrical anhydride by the action of oxalyl chloride reagent and a tertiary amine base (e.g. triethylamine) in a solvent such as $CH_2Cl_2$. The resultant anhydride is condensed with compound (1) in the presence of a tertiary base (e.g. triethylamine) in a solvent such as $CH_2Cl_2$.

As shown in Example 1 below, a compound of formula (1) may be prepared by hydrogenating a compound of formula Y:

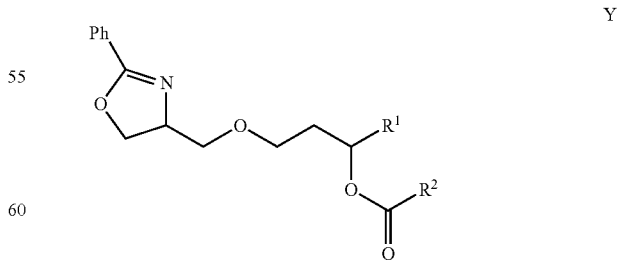

wherein $R^1$ and $R^2$ are as defined above. The hydrogenation may be carried out in any suitable solvent, e.g. ethanol, isopropanol and others known in the art, but preferably is done in isopropanol.

In formulas (1), (2), and (3), each of $R^1$, $R^2$ and $R^3$ may be, independently, for each occurrence a $C_5$-$C_{15}$ alkyl group, a $C_5$-$C_{15}$ alkenyl group, or a $C_5$-$C_{15}$ alkynyl group. The alkyl group, the alkenyl group, and the alkynyl group may be substituted or unsubstituted, straight or branched and is preferably a straight chain. In a preferred embodiment, $R^1$ is a $C_5$-$C_{12}$ alkyl group, a $C_5$-$C_{12}$ alkenyl group, or a $C_5$-$C_{12}$ alkynyl group and more preferably a $C_5$-$C_9$ alkyl group, a $C_5$-$C_9$ alkenyl group or a $C_5$-$C_9$ alkynyl group, while $R^2$ and $R^3$ each is, independently for each occurrence, a $C_7$-$C_{14}$ alkyl group or a $C_7$-$C_{14}$ alkenyl group and more preferably a $C_9$-$C_{13}$ alkyl group or a $C_9$-$C_{13}$ alkenyl group. Preferably, $R^1$ is a $C_7$ alkyl group, most preferably unsubstituted n-heptyl group, and $R^2$ and $R^3$ are both a $C_{11}$ alkyl group, most preferably an unsubstituted n-undecyl group.

The alkyl, alkenyl, alkynyl groups mentioned for the various groups of $R^1$, $R^2$, and $R^3$ above discussed with regard to the invention may be substituted or unsubstituted. Examples of substituents include, but are not limited to, halo substituents, (e.g. F, Cl, Br, and I); a $C_1$-$C_6$ alkoxy group, (e.g, —OCH$_3$, —OCH$_2$CH$_3$, —OCH(CH$_3$)$_2$, and the like); a $C_1$-$C_6$ haloalkyl group, (e.g., —CF$_3$, —CH$_2$CF$_3$, —CHCl$_2$, and the like); a $C_1$-$C_6$ alkylthio; an amide; —NO$_2$; and —CN.

Unless otherwise specified, the alkyl, alkenyl, and akynyl groups may be straight chains or branched with straight chains being generally preferred.

The β-keto amide alcohol compounds of formula (3) are novel compounds and are useful as, inter alia, intermediates in the preparation of compounds such as E6020. Compounds of formula (3) are a separate embodiment of the invention. β-keto amide alcohol compounds having the stereochemistry shown in formula (3a) are particularly preferred.

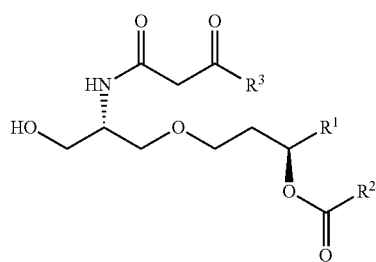

(3a)

In the synthesis of E6020, the β-keto amide alcohol is Compound 22. Compound 22 and its crystalline form are also separate embodiments of the invention. The synthesis of Compound 22 starting from Compound 14 is described below in Example 1, and the solid state characterization of crystalline 22 is described below in Example 2.

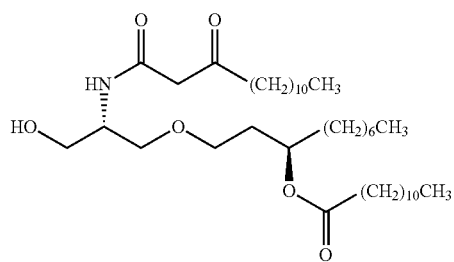

Compound 22

Preparation of a Urea Di-Phosphoramidite (4).

The urea di-phosphoramidite compounds of formula (4) represent another novel intermediate compound in the β-keto amide alcohol synthesis of E6020. Therefore compounds of formula (4) are a separate embodiment of the invention. The urea di-phosphoramidite compounds of formula (4) may be prepared by reacting a 1,3-bis(2-hydroxyethyl)urea with two phosphorodiamidite compounds of formula (7) as shown in Scheme 6, where $R^4$, $R^5$, and $R^6$ are as described below.

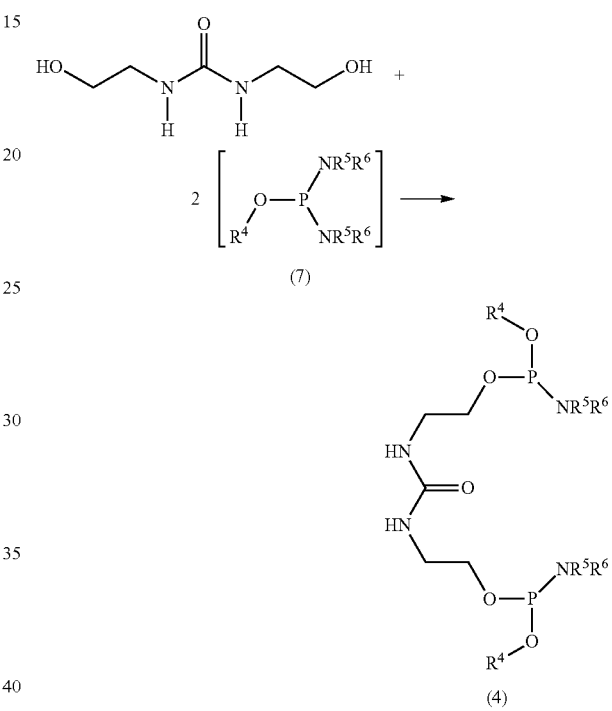

Scheme 6

In some embodiments, reaction of 1,3-bis(2-hydroxyethyl) urea with a phosphorodiamidite is effected by reacting the bis-hydroxy compound with a suitable activating agent such as is known to those skilled in the art, and then adding the phosphorodiamidite compound to the reaction mixture. In some embodiments, the activating agent is chosen from the group consisting of (1H)-tetrazole and pyridinium trifluoroacetate. In some embodiments, the activating agent is pyridinium trifluoroacetate. In some embodiments, the reaction of Scheme 6 is run in a solvent comprising a solvent selected from the group consisting of acetonitrile, dichloromethane, dichloroethane, and tert-butylmethyl ether. In some embodiments, the reaction of Scheme 6 is run in acetonitrile as a solvent.

Condensation of β-Keto Amide Alcohol (3) with Urea Di-Phosphoramidite (4).

As shown in Scheme 4 above, the synthesis of Compound 26 involves a condensation reaction of a β-keto amide alcohol of formula (3) with a urea di-phosphoramidite compound of formula (4) to form a β-keto amide urea phosphite compound of formula (5) which may then be oxidized to form a β-keto amide urea phosphate compound of formula (6). This is shown in Scheme 7 below.

Scheme 7

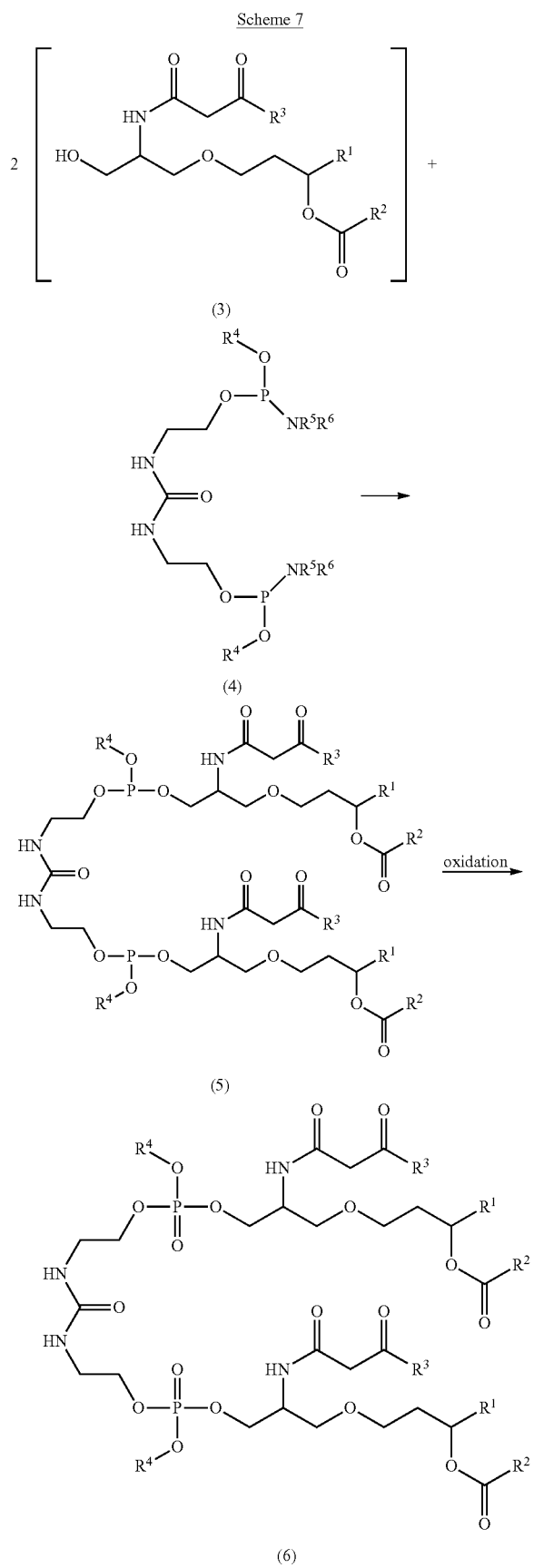

In formulas (4), (5), and (6), $R^1$, $R^2$ and $R^3$ are the same as described above, including their preferred embodiments, and are independent of one another. In each occurrence, $R^1$, $R^2$ and $R^3$ may be the same or different. In other words, a compound of formula (6) may have the same or different alkyl, alkenyl and/or alkynyl groups at each $R^1$, $R^2$ or $R^3$ position. Each $R^4$ group may independently be a protecting group, including but not limited to the following groups: an alkyl or substituted alkyl group such as methyl, ethyl, isopropyl, tert-butyl, and the like, preferably a $C_1$-$C_6$ alkyl group; an alkenyl or substituted alkenyl group such as allyl, 2-methyl propenyl, butenyl, and the like, preferably a $C_3$-$C_5$ alkenyl group; an alkynyl, preferably a $C_3$-$C_5$ alkynyl group; a cycloalkyl group such as cyclohexyl; a 2-substituted ethyl group such as 2-cyanoethyl, 2-cyano-1,1-dimethylethyl, 2-(trimethylsilyl)ethyl, and the like; a haloethyl group such as 2,2,2-trichloroethyl, 2,2,2-trichloro-1,1-dimethylethyl, 2,2,2-tribromoethyl, and the like; a benzyl or substituted benzyl group such as benzyl, 4-nitrobenzyl, 4-chlorobenzyl, and the like; an aryl or substituted aryl group such as phenyl, 4-nitrophenyl, 4-chlorophenyl, 2-chlorophenyl, 2-methylphenyl, 2,6-dimethylphenyl, 2-bromophenyl, and the like; and a silyl group such as trimethylsilyl and the like. Particularly preferred protecting groups for $R^4$ are methyl, ethyl, tert-butyl, allyl, 2-methyl propenyl, butenyl, 2-cyanoethyl ($NCCH_2CH_2$—), 2-(trimethylsilyl)ethyl (($CH_3$)$_3$Si$CH_2CH_2$—), and 2,2,2-trichloroethyl ($Cl_3CCH_2$—). Like $R^1$, $R^2$ and $R^3$, each occurrence of $R^4$ may vary from one another within the definition of $R^4$.

$R^5$ and $R^6$ are in each occurrence independently a $C_1$-$C_6$ alkyl group, a $C_3$-$C_6$ alkenyl group or a $C_3$-$C_6$ alkynyl group, wherein said alkyl, alkenyl, and alkynyl group may be substituted or unsubstituted, or, taken together with the nitrogen to which they are attached, form a 5- or 6-membered heterocyclic ring. The heterocyclic ring may include additional heteroatoms, e.g., N, O, and/or S; may be saturated or unsaturated, and may be unsubstituted or substituted. Examples of substituents include, but are not limited to, halo substituents, (e.g. F, Cl, Br, and I); a $C_1$-$C_6$ alkoxy group, (e.g, —$OCH_3$, —$OCH_2CH_3$, —$OCH(CH_3)_2$, and the like); a $C_1$-$C_6$ haloalkyl group, (e.g., —$CF_3$, —$CH_2CF_3$, —$CHCl_2$, and the like); a $C_1$-$C_6$ alkylthio; a —$NO_2$ group; and a —CN group. Suitable heterocyclic groups include, but are not limited to, piperidyl, morpholinyl, thiomorpholinyl, pyrrolidyl, and the like. The alkyl, alkenyl, and alkynyl groups of $R^4$, $R^5$ and $R^6$ may be substituted or unsubstituted, straight or branched. Examples of substituents include, but are not limited to, halo substituents, (e.g. F, Cl, Br, and I); a $C_1$-$C_6$ alkoxy group, (e.g, —$OCH_3$, —$OCH_2CH_3$, —$OCH(CH_3)_2$, and the like); a $C_1$-$C_6$ haloalkyl group, (e.g., —$CF_3$, —$CH_2CF_3$, —$CHCl_2$, and the like); a $C_1$-$C_6$ alkylthio; a —$NO_2$ group; and a —CN group. In a preferred embodiment, $R^4$ is a $C_3$-$C_5$ alkenyl group and $R^5$ and $R^6$ are each independently a branched $C_1$-$C_6$ alkyl group. Preferably, $R^4$ is an allyl group and $R^5$ and $R^6$ are isopropyl groups.

In some embodiments the compound of formula (3) is reacted with the compound of formula (4) by adding solvent to the mixture of compound of formula (3) and the compound of formula (4), stirring until all solids are dissolved, and adding acetic acid to the mixture. In some embodiments, the solvent is anhydrous and may be a co-solvent mixture. In some embodiments, the co-solvent mixture comprises acetonitrile and a hydrocarbon solvent and in a preferred embodiment, the solvent may be, for example, a mixture of anhydrous acetonitrile and anhydrous heptane. In some embodiments the co-solvent mixture comprises heptane and acetonitrile. In some embodiments, the weight of heptane in the co-solvent mixture is between 4 and 6 times the weight of the compound of formula (3). In some embodiments, the weight of heptane in the co-solvent mixture is between 4.5 and 5.5 times the weight of the compound of formula (3). In some embodiments the weight of acetonitrile in the co-solvent mixture is between 1 and 2 times the weight of the compound of formula (3). In some embodiments the weight of acetonitrile in the co-solvent mixture is between 1.2 and 1.5 times the weight of the compound of formula (3). In some embodiments, the weight of acetic acid used is between 1 and 2 molar equivalents of the amount of the compound of formula (3) used. In some embodiments, the amount of acetic acid used is between 1.2 and 5 molar equivalents of the amount of the compound of formula (3) used. In some embodiments, the temperature of the reaction mixture is maintained at about 20-25° C. during the addition of acetic acid.

In some embodiments, the compound of formula (5) formed by the method of Scheme 7 is oxidized to the compound of formula (6) by an oxidizing agent. In some embodiments, the oxidizing agent is hydrogen peroxide, Oxone® oxidant, mCPBA (meta-chloro perbenzoic acid), and the like. In some embodiments the hydrogen peroxide is 30% (wt/wt) $H_2O_2$ in water. In some embodiments, the reaction mixture containing the formed compound of formula (5) is diluted with additional heptane before the oxidation step. In some embodiments, the weight of the additional heptane added is between 5 and 10 times the weight of the compound of formula (3) used. In some embodiments, the weight of the additional heptane added is about 8 times the weight of the compound of formula (3) used. In some embodiments, the reaction mixture containing the formed compound of formula (5) is cooled to about −5-10° C. after adding the additional heptane and before adding the oxidizing agent. In some embodiments, the reaction mixture containing the formed compound of formula (5) is cooled to about 0-5° C. after adding the additional heptane and before adding the oxidizing agent. In some embodiments, the temperature of the reaction mixture is maintained at about −5-10° C. after adding the oxidizing agent. In some embodiments, the temperature of the reaction mixture is maintained at about 0-2° C. after adding the oxidizing agent. In some embodiments, the reaction is stirred at a temperature about −5-10° C. following addition of the oxidizing agent until the reaction is complete. In some embodiments, the reaction is stirred at a temperature about −1-2° C. following addition of the oxidizing agent until the reaction is complete. In some embodiments, the reaction is monitored by HPLC to determine completion. In some embodiments, the reaction is quenched with sodium thiosulfate pentahydrate to destroy excess peroxides after the reaction is complete.

In the synthesis of Compound 26, the compound of formula (4) is Compound 25. Compound 25 and its crystalline form are also separate embodiments of the invention. The synthesis of Compound 25 starting from the dihydroxy urea Compound 24 is described below in Example 4, and the solid state characterization of crystalline Compound 25 is described below in Example 5.

Example 6 below describes the preparation of E6020 precursor Compound 26 (a species of the compounds of formula (6) where $R^1$ is n-heptyl, $R^2$ and $R^3$ are both n-undecyl, and $R^4$ is allyl) from the reaction of Compound 22 and Compound 25.

The synthetic method described herein may be adapted to the preparation of any of all possible stereoisomers of Compound 26 and correspondingly E6020, e.g., compounds (A) and (B) respectively below having the general structures:

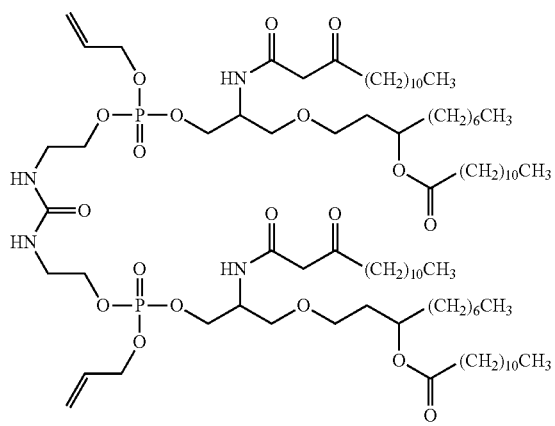

A

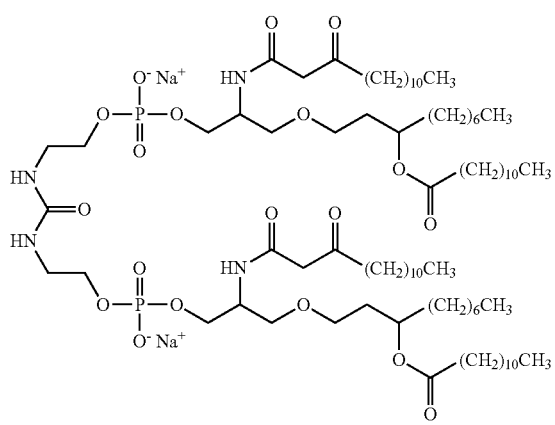

B

While the examples below disclose the preparation of a particular stereoisomer, methods for preparing other stereoisomers of Compound 26 are considered to fall within the scope of the present invention. The synthetic method of the invention is well suited to provide pure stereoisomers for which the initial stereochemistry of the starting material (3) is defined and used in a 2 equivalent ratio to the urea di-phosphoramidite (4) as shown in Scheme 7 (above). This method would allow one to prepare four pure stereoisomers including E6020 with a (R,R,R,R) stereochemistry at positions 1, 6, 22, 27; ER-824156 (S,S,S,S); ER-804053 (R,S,S,R); and ER-824095 (S,R,R,S). To prepare the other stereoisomers (ER-826685 (R,R,S,R); ER-824887 (R,R,R,S); ER-826682 (R,R,S,S); ER-827905 (R,S,R,S); ER-826683 (R,S,S,S); ER-804097 (S,S,R,S)) one would obtain a mixture of products for which one would use 1 equivalent of starting material (3) with a defined stereochemistry at positions 2 and 7 while a second equivalent of starting material (3) would have a differently defined stereochemistry at positions 2 and 7. The resultant reaction (using Scheme 7) would provide 3 different stereoisomers of compound (6) that can be separated by column chromatography and structurally determined by $^1$H-NMR and HPLC comparison to authentic stereoisomers previously prepared by the first synthetic method described above and a separate method as described in U.S. Pat. No. 6,290,973. U.S. Pat. Nos. 6,551,600; 6,290,973; and 6,521,776, which disclose other synthetic routes to E6020 and related compounds, provide helpful background information on preparing certain reagents and starting materials and are incorporated herein by reference.

EXAMPLES

In the examples below, when the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like). The term "equivalent" (abbreviation: eq) as used herein describes the stoichiometry (molar ratio) of a reagent or a reacting compound by comparison to a pre-established starting material. The term "weight" (abbreviation: wt) as used herein corresponds to the ratio of the mass of a substance or a group of substances by comparison to the mass of a particular chemical component of a reaction or purification specifically referenced in the examples below. The ratio is calculated as: g/g, or Kg/Kg. The term "volume" (abbreviation: vol) as used herein corresponds to the ratio of the volume of a given substance or a group of substances to the mass or volume of a pre-established chemical component of a reaction or purification. The units used in the equation involve matching orders of magnitude. For example, a ratio is calculated as: mL/mL, mL/g, L/L or L/Kg. The following abbreviations are used herein:

| Abbreviation | Chemical |
|---|---|
| ACN | acetonitrile |
| Boc | tert-butoxycarbonyl |
| CDI | carbonyldiimidazole |
| DMAP | 4-(dimethylamino)pyridine |
| DMF | dimethylformamide |
| EDC | (N-(3-dimethylaminopropyl)-N-ethyl carbodiimide hydrochloride) |
| EtOH | ethanol |
| Et$_3$N | triethylamine |
| Fmoc | 9-fluorenylmethoxycarbonyl |
| NaHMDS | sodium hexamethyldisilazide |
| HOAc | acetic acid |
| IPA | isopropyl alcohol |
| iPr | isopropyl |
| Pd/C | palladium on carbon |
| Pd(PPh$_3$)$_4$ | tetrakis(triphenylphosphine)palladium (0) |
| PPh$_3$ | triphenylphosphine |
| PhSiH$_3$ | phenylsilane |
| Py | pyridine |
| Py•TFA | pyridinium trifluoroacetate |
| TBME | tert-butyl methyl ether |
| TFA | trifluoroacetic acid |
| TFFH | fluoro-N,N,N',N'-tetramethylformamidinium hexafluorophosphate |
| THF | tetrahydrofuran |
| TM | Test Method |
| TsCl | tosylchloride |

Example 1

Preparation of Compound 22

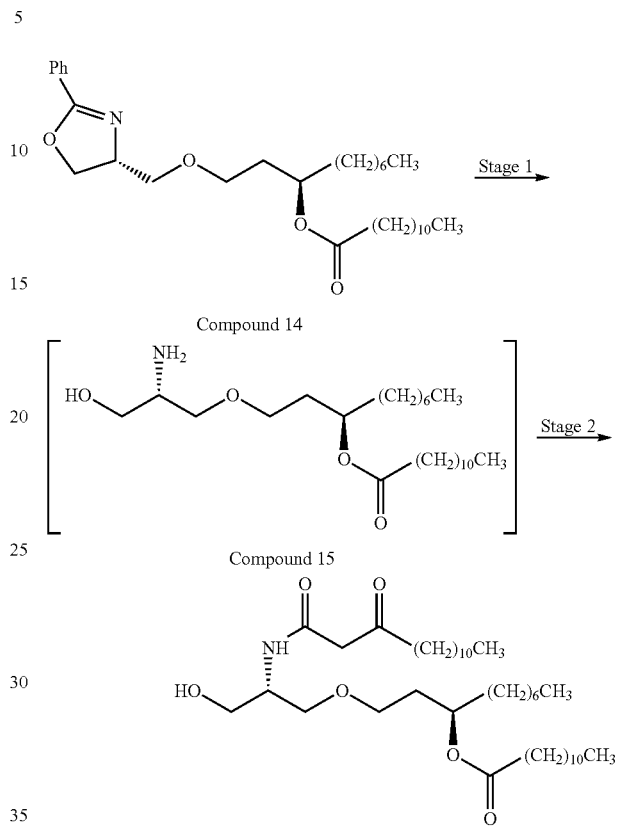

Preparation of Compound 15 (Step 1)

General Procedure: As shown in Stage 1 above, Compound 15 may be prepared as follows. To an inerted reaction vessel is added Compound 14 (1 wt, 1 eq), Pd/C (preferably approximately 0.1-0.2 wt, 0.025-0.050 eq), and an appropriate hydrogenation solvent (e.g., a non-aqueous polar solvent such as THF, preferably a polar protic solvent, more preferably a low molecular weight alcohol; most preferably ethanol or isopropanol) (approximately 6-7 vol). The inert gas in the vessel is replaced with hydrogen, (preferably at a pressure of approximately 1 atmosphere to approximately 120 psi) and the reaction mixture is stirred at room temperature until the reaction is essentially complete (approximately 3-8 days). Hydrogen in the reaction vessel is then replaced with an inert gas and the catalyst is removed by filtration (e.g., using Celite). The filtrate is then concentrated to yield Compound 15 (approximately 0.8 wt) as a pale yellow oil. The following procedures describe the hydrogenation of Compound 14 to Compound 15 in ethanol and in isopropanol.

Step 1(a1): Hydrogenation in Ethanol: To an inerted round bottom flask equipped with a magnetic stirring device was added Compound 14 (3.00 g, 1.0 wt, 1.0 eq), 10% Pd/C (Degussa type E101 NE/W, 0.300 g, 0.10 wt, 0.024 eq, Aldrich), and ethanol (20.0 mL, 6.7 vol). The inert gas in the vessel, nitrogen, was replaced with hydrogen (1 atmosphere) and the reaction mixture was stirred at room temperature until the reaction was found complete by TLC analysis (approximately 4 days). Hydrogen in the reaction vessel was then replaced with nitrogen, the catalyst was removed by filtration on Celite and a small amount of ethanol was used as rinse.

Step 1(a2) Compound 15 may generally be used in situ to prepare Compound 22. For characterization purposes, the Compound 15/ethanol filtrate was concentrated to yield Compound 15 (2.5 g, 0.83 wt) as a pale yellow oil, redissolved in a minimum amount of 10% methanol/dichloromethane, loaded onto a silica gel column (KP-Sil, 13.0 wt), and eluted with 10% methanol/dichloromethane. A few pure fractions were combined and concentrated in vacuo to give purified Compound 15 (0.1 wt).

Analytical Data for purified Compound 15: $^1$H NMR (400 MHz, CDCl$_3$) δ: 5.03-5.10 (m, 1H), 3.63 (dd, J=10, 5 Hz, 1H), 3.42-3.52 (m, 3H), 3.34-3.39 (m, 2H), 3.02-3.07 (m, 1H), 2.29 (t, J=7 Hz, 3H), 1.73-1.94 (m, 6H), 1.48-1.66 (m, 4H), 1.20-1.36 (m, 26H), 0.89 (t, J=7 Hz, 6H). ESI-MS (M+H)$^+$ Theoretical calculation for $C_{25}H_{52}NO_4$: 430.4; actual result: 430.4.

Step 1(b1) Hydrogenation in Isopropanol: To an inerted 12-L glass flask were charged Compound 14 (2.0 kg, 1.0 wt) and isopropanol (8.0 kg, 4.0 wt), and the mixture was stirred until the Compound 14 was dissolved. To a 5-gallon inerted reactor equipped with mechanical stirring were charged Pd/C (Johnson Matthey type A402028-10, 10% Pd/C, 50% wet; 0.411 kg, 0.206 wt, 0.05 eq) and the Compound 14/isopropanol solution. Isopropanol (1.1 kg, 0.55 wt) was used to rinse residual Compound 14 into the 5-gallon reactor. The 5-gallon reactor was then pressurized with nitrogen to 10-15 psi while stirring at ~750 rpm. Nitrogen was vented while stirring at ~250 rpm. The nitrogen-pressurization-and-venting cycle was repeated two more times. The reactor was pressurized with hydrogen (grade 5.0) to 25 psi while stirring at ~750 rpm, and the hydrogen was then vented while stirring at ~250 rpm. The reactor was then pressurized with hydrogen to 120 psi while stirring at ~750 rpm. The reaction mixture was then stirred at ambient temperature for 65 h, after which the hydrogen was vented. The reactor was then pressurized with nitrogen to 10-15 psi, after which the nitrogen was vented. The nitrogen-pressurization-and-venting process was repeated two more times. HPLC monitoring showed a complete reaction. The catalyst was then removed by filtration through two CUNO filter housings (a CUNO CTG Klean 1.0 μm filter cartridge and a CUNO CTG Klean 0.2 μm filter cartridge connected in series) that had been pre-washed with isopropanol (3.9 kg, 1.95 wt). The reactor was rinsed with isopropanol (5.0 kg, 2.5 wt) and the resultant rinse solution was filtered through the CUNO housings. The filtrates were combined and produced an Compound 15/isopropanol colorless clear solution (15.8 kg, 7.9 wt). Approximately 15 kg (7.5 wt) (=0.95×15.8 and 7.9, respectively) of this solution was concentrated at reduced pressure to 6.55 kg (3.28 wt), and used in the Step 2a without purification.

Preparation of Compound 22 (Step 2a)

General Procedure: As shown in Stage 2 above, the following general procedure may be used to prepare Compound 22 (all weights, equivalents and volumes are relative to the mass of Compound 14 used in Step 1): Into an inerted glass reactor equipped with a stirring device is charged carbonyldiimidazole (CDI) (0.34 wt, 1.1 eq) and anhydrous acetonitrile (7.4 wt). Stirring is initiated and the mixture is cooled to about 0° C. 3-oxo-tetradecanoic acid (0.514 wt, 1.1 eq) is added and stirring is continued while the temperature is maintained at about 0° C. The imidazolide formation is monitored by HPLC. When determined complete, the Compound 15/IPA solution (3-8 wt) obtained in Step 1 is added, keeping the temperature at around 0° C. The reaction mixture is stirred at around 0° C. and monitored by HPLC. After completion, glacial acetic acid (0.24 wt, 2.1 eq) is added while keeping the reaction temperature ≦15° C. The reaction mixture is brought to about 20° C. and its volume reduced to about 5-7.5 vol by partial solvent evaporation in vacuo at 20-25° C., giving a clear orange solution. Heptane (8.5 wt) is added and the resultant mixture is washed with a solution composed of NH$_4$Cl (0.15 wt) and water (5.2 wt). The heptane layer is then washed with a solution composed of sodium chloride (1.0 wt) and water (3.2 wt). The heptane layer is concentrated in vacuo at about 25-30° C. down to about 2.2-4.4 vol, then isopropyl acetate (9.0 wt) is added and the resultant solution is concentrated in vacuo at about 25-30° C. to give a clear orange oil (2.2-5.6 vol or 2.0-5.0 wt).

Specific example: The following procedure describes the preparation of Compound 22 on a scale that involved 95% of the amount of Compound 15 produced using 2.0 Kg of Compound 14 in Step 1(b1). Thus for this example, 1.9 Kg=1.0 wt. In a 50 L inerted glass reactor equipped with a mechanical stirrer was charged carbonyldiimidazole (CDI) (0.65 Kg, 0.34 wt, 1.1 eq) and anhydrous acetonitrile (14.1 Kg, 7.4 wt). Stirring was initiated and the mixture was cooled to 0° C. Then, 3-oxo-tetradecanoic (0.98 Kg, 0.516 wt, 1.1 eq.; purchased from DSM Pharmaceutical Products, Parsippany, N.J.) was added under continued stirring, while maintaining the temperature at about 0° C. The imidazolide formation was monitored by HPLC. Upon completion, after approximately 10.5 h, the Compound 15/IPA solution (6.55 kg, 3.45 wt) obtained in Step 1(b1) was added over 1 min and the temperature remained around 0° C. IPA (1.7 Kg, 0.89 wt) was used as rinsing solvent. The reaction mixture was stirred overnight at 0-3° C. HPLC confirmed that the reaction was complete. Glacial acetic acid (0.46 Kg, 0.24 wt, 2.1 eq) was then added while keeping the reaction temperature ≦15° C. (The acetic acid addition took place approximately 12.25 h after the Compound 15 addition.) The reaction mixture was brought to 20° C. and its volume was reduced to about 13 L (6.8 vol) by partial solvent evaporation in vacuo at 20-22° C., which produced a clear orange solution. Heptane (16.2 Kg, 8.53 wt) was added and the resultant mixture was washed with a solution composed of NH$_4$Cl (0.29 Kg, 0.15 wt) and water (9.9 Kg, 5.2 wt) followed by washing with a solution composed of sodium chloride (1.9 Kg, 1.0 wt) and water (6.1 Kg, 3.2 wt). The heptane layer was concentrated in vacuo at 25-30° C. down to ~7 L (3.7 vol). Isopropyl acetate (17.0 Kg, 8.95 wt) was then added and the resultant solution was concentrated in vacuo at 25-30° C., which produced a clear orange oil ~7 L (3.7 vol, Purity (HPLC): 83.8 area %). HPLC conditions for analysis of Compound 22 (HPLC TM1 of Compound 22):

| HPLC Column | Waters Xterra RP18, 150 × 4.6 mm, 5 μm, Waters catalog 186000492 |
|---|---|
| Temperature | 35° C. |
| Mobile phase | A: 2.0 mL of 28-30% aqueous NH$_4$OH in 1 L of water, B: 2.0 mL of 28-30% aqueous NH$_4$OH in 1 L of CH$_3$CN |
| Flow Rate | 1.0 mL/min |
| | time, min  %-Solvent B |
| Gradient | initial  93 |
| | 15  93 |
| | 18  100 |
| | 27  100 |
| Injection Volume | 10 μL |
| Detection (UV) | 225 nm |
| Compound 22 Retention time | 9.4 min ± 10% |

Compound 22 Crystallization (Step 2b)

General Procedure: Compound 22 may be crystallized from an isopropyl acetate/acetonitrile mixture. For example, in a glass vessel, Compound 22 (2.2-5.6 vol, based on Compound 14) is dissolved in isopropyl acetate (3.5 wt). The resultant solution is filtered and adjusted to a total weight of about 7.4 wt with isopropyl acetate. The solution is then transferred to an appropriately sized jacketed glass reactor equipped with a stirring device and acetonitrile (5.0 wt) is added. Under inert nitrogen atmosphere, the resultant mixture is cooled to about 5-8° C. to form Compound 22 crystals. The temperature is warmed to about 15° C. to dissolve smaller crystals. The temperature is held at 15° C. for about 2 h, slowly cooled to about −12° C., and then preferably held at −12° C. for an additional 1 h. Compound 22 is filtered and the solid rinsed with a cold (~−20° C.) mixture of isopropyl acetate/acetonitrile (1:1 (v/v), 1-2 wt). The wet cake is dried to produce Compound 22 as a white solid (approximately 0.9-1.5 wt).

Specific example: The following procedure presents how Compound 22 was crystallized out on a scale that involved 1.9 Kg of Compound 14 starting material (i.e., 1.9 Kg=1.0 wt): In a glass vessel, the crude Compound 22 oil from Step 2a (3.7 vol based on Compound 14) was dissolved in isopropyl acetate (6.7 Kg, 3.5 wt). The resultant solution was filtered and excess solvent was removed in vacuo at 25-30° C. The remaining solution (7.23 Kg, (3.8 wt)) was then transferred to a 50 L jacketed glass reactor equipped with a mechanical stirrer and the mass adjusted to about 14.0 Kg (7.4 wt) by the addition of isopropyl acetate (6.27 Kg, 3.3 wt). Acetonitrile (9.6 Kg, 5.1 wt) was then added. Under inert nitrogen atmosphere, stiffing was initiated and the resultant mixture was cooled to 7.3° C. to form Compound 22 crystals. The temperature was then raised to 15.1° C. to dissolve smaller crystals. The temperature was held at 15° C. for about 2 h, slowly cooled to −11.7° C. overnight, and then held at around −12° C. for about 1 h. The resulting composition was filtered and the solid was rinsed with a cold (~−20° C.) mixture of isopropyl acetate/acetonitrile (1:1 (v/v), 2.6 Kg, 1.4 wt). The wet cake was dried in vacuo, which produced Compound 22 as a white solid, (1.83 Kg, 0.96 wt; Purity: 92.5 area % (HPLC TM1 of Compound 22); Yield: 69% from Compound 14).

Compound 22 Recrystallization (Step 2c)

General Procedure: In an appropriately sized and inerted jacketed glass reactor equipped with a stiffing device are combined Compound 22 (1.0 wt (based on Compound 22)), isopropyl acetate (4.4-4.9 wt) and acetonitrile (3.9-4.5 wt). The resultant mixture is stirred and warmed to 20-25° C. to give a clear solution. The clear solution is cooled to 5-10° C. to form crystals. The temperature is then warmed to 16-20° C. to dissolve smaller crystals and held at about 17° C. for about 2 h. The temperature is slowly cooled linearly to about −3 to −8° C. over about 10-11 h. Preferably the temperature is held at −3 to −8° C. for an additional 2 h. The solid is filtered and rinsed with a cold (−20° C.) solution of isopropyl acetate/acetonitrile (1:1 (v/v), 1-3 wt) and dried in vacuo to produce Compound 22 as a white powder, (approximately 0.8-0.95 wt).

Specific Example: The following procedure describes the recrystallization of Compound 22: 1.79 Kg of Compound 22 from the crystallization in Step 2b (@92.5% purity=1.65 Kg compound; 1.65 Kg=1.0 wt) were combined with isopropyl acetate (8.0 Kg, 4.8 wt) and acetonitrile (7.37 Kg, 4.5 wt) in an inerted 30 L jacketed glass reactor equipped with a mechanical stirrer. The resultant mixture was stirred and warmed to 24.3° C. to give a clear solution. The clear solution was cooled to 10.4° C. to form crystals. Then, to dissolve smaller crystals, the temperature was warmed to 16.2° C. and was held at 16.2-17.3° C. for about 2 h. The temperature was slowly cooled to −3.4° C. overnight. The following day, the temperature was held at that temperature for an additional 20 min. The solid was filtered and rinsed with a cold (~−20° C.) solution of isopropyl acetate/acetonitrile (1:1 (v/v), 4.6 Kg, 2.8 wt) and dried in vacuo (18-25° C., 5 h), which produced Compound 22 as a white solid, (1.54 Kg, 0.93 wt; Purity: 99.4% (HPLC TM1 of Compound 22); Yield: 92.8%).

Analytical Data for Compound 22: $^1$H NMR (400 MHz, $CDCl_3$) δ: 7.24 (d, J=7 Hz, 1H), 5.05-5.14 (m, 1H), 4.03-4.11 (m, 1H), 3.72 (dd, J=5, 5 Hz, 2H), 3.42-3.60 (m, 3H), 3.41 (s, 2H), 3.26-3.38 (m, 1H), 2.53 (t, J=7 Hz, 3H), 2.29 (t, J=7 Hz, 3H), 1.79-1.89 (m, 1H), 1.48-1.77 (m, 7H), 1.19-1.38 (m, 42H), 0.88 (t, J=7 Hz, 3H). ESI-MS $(M+H)^+$ Theoretical calculation for $C_{39}H_{76}NO_6$: 654.6; actual result: 654.6.

Example 2

Solid State Characterization of Crystalline Compound 22

A. Powder X-Ray Diffraction

Figure 2:
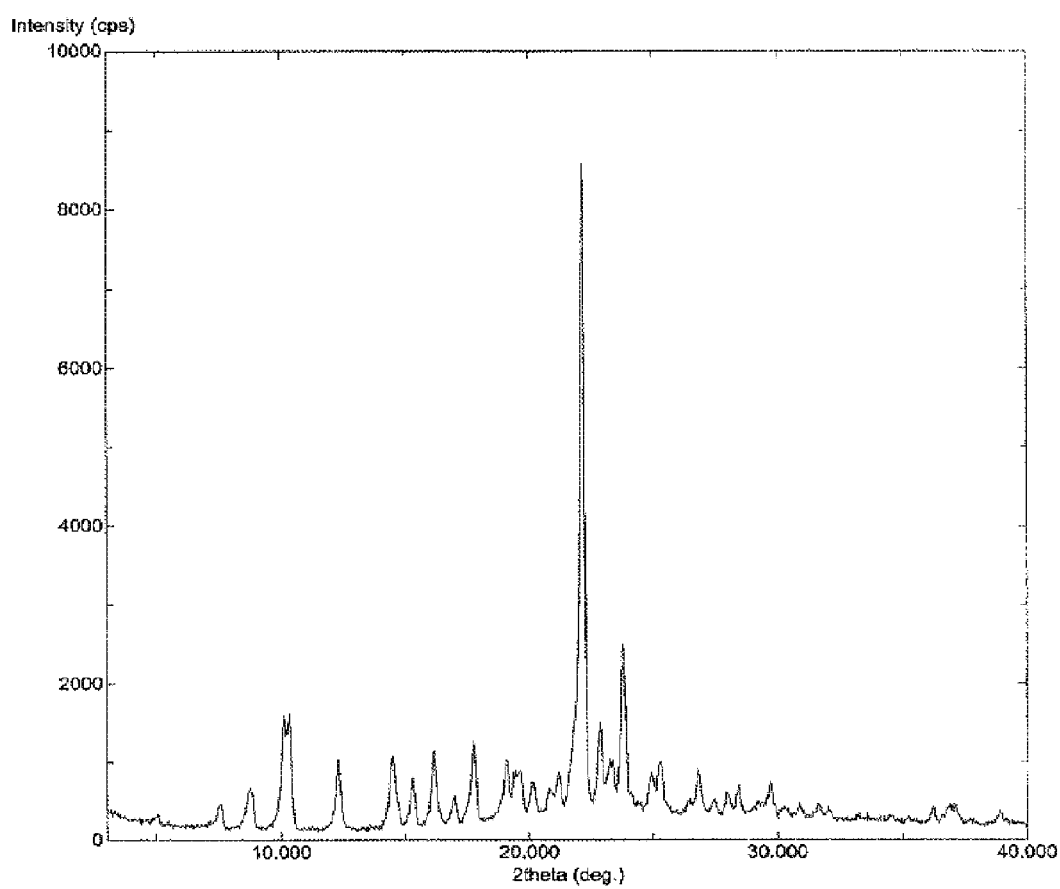
FIG. 2 is the powder X-ray diffraction pattern of crystalline Compound 22.

Using a glass plate, on the Scintag Diffractometer, data were collected under normal powder diffraction conditions, with 2-theta range of 3-40 degrees, using copper radiation. No background correction was applied. FIG. 2 shows the PXRD pattern of crystalline Compound 22. The PXRD pattern shows peaks at 10.3±0.2°2Θ, 12.3±0.2°2Θ, 14.5±0.2°2Θ, 15.3±0.2 ° 2Θ, 16.2±0.2°2Θ, 17.8±0.2°2Θ, 22.2±0.2°2Θ, 22.9±0.2°2Θ, 23.8±0.2°2Θ, 25.3±0.2°2Θ, and 26.8±0.2°2Θ. Crystalline Compound 22 may be characterized by a subset of the peaks shown in FIG. 2. For example, the following peaks are characteristic of crystalline Compound 22: 12.3±0.2°2Θ, 14.5±0.2°2Θ, 16.2±0.2°2Θ, 17.8±0.2°2Θ, 22.2±0.2°2Θ, and 23.8±0.2°2Θ. Other combinations of the peaks listed or shown in FIG. 2 may also be used to identify Compound 22.

TABLE 1

| Measurement conditions | |
|---|---|
| X-ray diffractometer: | Scintag |
| Target: | Cu |
| Detector: | Scintillation Counter |
| Tube voltage: | 40 kV |
| Tube current: | 20 mA |
| Slit: | DS 1°, RS 0.3 mm, SS 1° |
| Scan speed: | 2°/min |
| Sampling width: | 0.02° |
| Scan range: | 3 to 40° |
| Sample holder: | glass holder |
| Goniometer: | horizontal goniometer |
| Filter: | not used |

B. DSC Characterization

Figure 3:
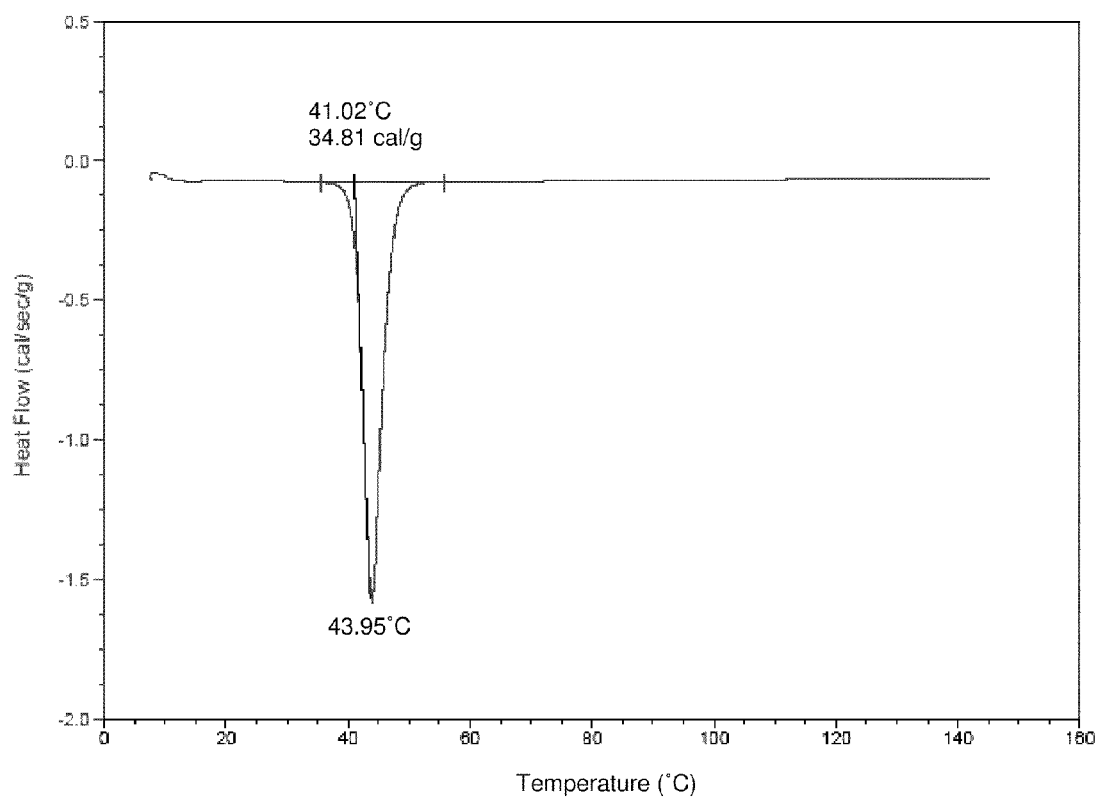
FIG. 3 is the DSC thermogram of crystalline Compound 22.

Solid-state characterization of crystalline Compound 22 was determined by Differential Scanning calorimetry (DSC, aluminum pan technique). The DSC was run with a 2920 DSC V2.5F calorimeter heating to 150° C. at 10° C./min with an aluminum pan under a nitrogen purge of 50 mL/min using a 2.91 mg sample of crystalline Compound 22. FIG. 3 shows the thermogram of crystalline Compound 22 with melting at 41° C. (onset temp.).

A melting point experiment was also conducted using an Electrothermal Mel.Temp Apparatus, with a Fluke 51 II Digital Thermometer. Compound 22 (2-3 mg) was loaded in a capillary tube (1.5-1.8×90 mm, Kimble Product KIMAX-51, part no. 34505). The observed melting point was 41-42° C.

Example 3

Compound 25 Synthesis and Seed Crystals Formation

A. Compound 25 Synthesis and Crude Crystals Preparation (Step 3a)

Synthesis of Compound 25: Into an inerted jacketed glass reactor equipped with a mechanical stirrer were added Compound 24 (N,N'-bis(2-hydroxyethyl)urea; 8.00 g, 1.00 wt, 1.00 eq; purchased from vendor Mitsui & Co. (USA), Inc., New York, N.Y.; manufacturer Yoyu Labs), pyridinium trifluoroacetate (0.5 g, 0.063 wt, 0.05 eq) and acetonitrile (59.7 g, 7.5 wt). Stirring was initiated and allyl tetraisopropylphosphorodiamidate (35.0 g, 4.4 wt, 2.24 eq; purchased from Digital Specialty Chemicals, Inc., Dublin, N.H.) was added. The resultant mixture was then stirred at 20-25° C. overnight (17 h). HPLC monitoring revealed a complete reaction. The temperature was cooled to 0° C., and a precipitate appeared. The temperature was slowly warmed to 16° C. over 2 h to dissolve most of the solid that had formed. The mixture was then stirred at 16° C. for 1.5 h, cooled to −17.4° C. at a rate of 5° C./h, and stirred overnight at that temperature, producing a thick suspension. The temperature was then raised to 16° C. over 2.3 h and maintained at 16° C. for 2.25 h. The temperature was dropped to 3.5° C. over 1.2 h and then quickly (approx. 5-10 min) warmed to 10° C. The temperature was held at 10° C. for 2 h and was cooled overnight at a rate of about 1.5° C./h to a final temperature of −16° C. The solid that had formed was filtered, washed with cold acetonitrile (2×6.3 g, 2×0.79 wt), and dried under vacuum. Compound 25 (19.7 g, 2.46 wt) was obtained as a white solid.

B. Compound 25 Recrystallization (Step 3b)

Into an inerted jacketed glass reactor equipped with a mechanical stirrer was added Compound 25 from Step 3a (19.5 g, 1.00 wt) and acetonitrile (55.0 g, 2.8 wt). The resultant mixture was stirred at 20-25° C. for 15 min. The temperature was cooled to 10° C., at which point stirring became difficult. The temperature was raised to 20° C. and maintained there for 2 h. Cooling to 10° C. was resumed at a rate of about 2° C./h. Cooling was continued to 1° C. a rate of about 3° C./h, followed by cooling to −19° C. at a rate of about 5° C./h. The solid that formed was filtered, washed with cold acetonitrile (32 g, 1.6 wt), and dried under vacuum. Compound 25 (16.06 g, 0.82 wt) was obtained as a white solid.

C. Compound 25 Seed Crystals Formation (Step 3c)

The following procedure can be and was used to prepare the seed crystals referenced in Step 4a and Step 4b, below: Into an inerted jacketed glass reactor equipped with a mechanical stirrer was added Compound 25 from Step 3b (5.59 g, 1.00 wt) and a solution composed of heptane and TBME (9:1 (v/v), 120 mL, 21.5 vol). The resultant mixture was stirred at 20-25° C., and more TBME (3.0 mL, 0.54 vol) was added to completely dissolve Compound 25. The temperature was reduced to 10° C. over about 1.5 h, forming a white precipitate. The temperature was warmed to 16° C. and maintained there for about 2 h. The reactor was cooled at a rate of about 2° C./h to 0° C., followed by cooling at a rate of about 3° C./h to −18.8° C., then maintained at about −18.8. This cooling profile was carried out overnight. The solid that formed was filtered, washed with a cold solution composed of heptane and TBME (9:1 (v/v), 16 g, 2.9 wt), and dried under vacuum. Compound 25 (5.23 g, 0.936 wt; Purity: 94.7% (area percent)) was obtained as a white solid. HPLC conditions for analysis of Compound 25 (HPLC TM2 of Compound 25)

| HPLC Column | Phenomenex Luna phenyl-hexyl, 250 × 4.6 mm, 5 μm. Catalog # 00G-4257-E0. |
|---|---|
| Mobile phase | A = water |
| | B = CH$_3$CN |
| Flow Rate | 1.0 mL/min |
| | time, min    %-Solvent B |
| Gradient | initial    2 |
| | 40.0    26 |
| | 75.0    100 |
| | 85.0    100 |
| Injection Volume | 3 μL |
| Detection (UV) | 200 nm |
| Compound 25 Retention time | 30 min ± 10% |

Example 4

Preparation of Compound 25

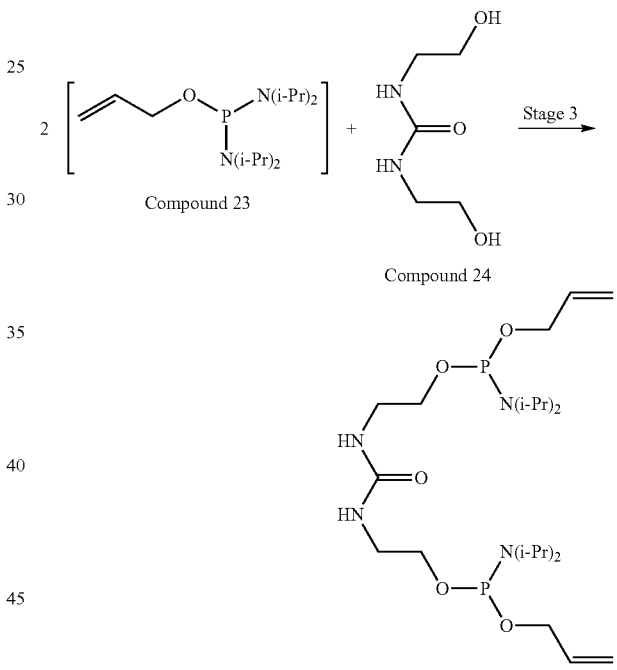

Stage 3: Py. TFA, ACN, crystallization.

Preparation of Compound 25 (Step 4a)

General Procedure to prepare Compound 25: (Note: 1.0 wt herein refers to the mass of Compound 24 used as starting material to produce a batch of Compound 25). In an appropriately sized and inerted jacketed glass reactor equipped with a stirring device are combined urea Compound 24 (1.0 wt, 1.0 eq), pyridinium trifluoroacetate (0.07 wt, 0.05 eq) and anhydrous acetonitrile (7.0 wt). Stirring is initiated and allyl tetraisopropylphosphorodiamidite (4.4 wt, 2.3 eq) is added. The reaction is stirred at 18-26° C. for several hours until complete. The resultant mixture is cooled to approximately 9-11° C., preferably seeded with crystalline Compound 25 (~0.005 wt; the preparation of the Compound 25 seed crystals is discussed in Example 3, above) and the temperature maintained for about 2 h. The mixture is then cooled to about 0 to −15° C. at a rate of about 1.5° C./hour, followed by cooling to about −20° C. at a rate of about 2.5° C./hour. After holding the temperature stable for about 2 hours, the solid is filtered under a nitrogen atmosphere, washed with cold (−20° C.) anhydrous acetonitrile (2-3 wt) and dried under nitrogen. Compound 25 (about 2.3-2.5 wt) is thus produced as a white solid. Compound 25 is preferably stored under dry nitrogen at low temperature (e.g., −20° C.) until purification.

Specific example: The procedure below describes the synthesis of Compound 25 starting from Compound 24 (0.50 Kg, referred herein as 1.0 wt): In a 30 L inerted jacketed glass reactor equipped with a mechanical stirrer were combined urea Compound 24 (0.50 Kg, 1.0 wt, 1.0 eq), pyridinium trifluoroacetate (0.035 Kg, 0.07 wt, 0.05 eq) and anhydrous acetonitrile (3.5 Kg, 7.0 wt). Stirring was initiated and allyl tetraisopropylphosphorodiamidite (2.22 Kg, 4.4 wt, 2.3 eq) was added. The reaction was stirred at 18.4-25.6° C. It was monitored by HPLC, which confirmed that the reaction was complete after 18 h. The resultant mixture was cooled to 11.1° C. and the temperature was kept at 9.3-11.1 C for about 50 min. The mixture was seeded with crystalline Compound 25 (1.9 g, 0.004 wt; the preparation of the Compound 25 seed crystals is discussed in Example 3, above) and kept in the 9-11° C. temperature range for about 2 h. The mixture was then cooled to −7.9° C. at a rate of about 1.5° C./hour. The cooling rate was then accelerated to about 2.5° C./hour and the temperature was brought to −18° C. The temperature was held at −18 to −19.2° C. for about 2 h, after which the solid that had formed was filtered under a nitrogen atmosphere, washed with cold (∼−20° C.) anhydrous acetonitrile (1.5 Kg, 3.0 wt), and dried under a stream of nitrogen. Compound 25 (1.18 Kg, 2.36 wt; Purity: 93.6% area percent (HPLC TM2 of Compound 25)) was obtained as a white solid and was stored under nitrogen at about −20° C. until purification.

Compound 25 Recrystallization (Step 4b)

General Procedure for the recrystallization of Compound 25: In an appropriately sized and inerted glass reactor equipped with a stiffing device, urea di-phosphoramidite Compound 25 (1.0 wt, 1.0 wt herein refers to the mass of crude Compound 25 precipitated from the reaction that produced it) is dissolved in TBME (1.5-2.0 wt). Insoluble particulates are removed by filtration. The filtrate is transferred to an appropriately sized and inerted jacketed glass reactor equipped with a stiffing device. Heptane (13.2 wt) is added, and the resultant solution is cooled to about 9-11° C. and stirred in that temperature range for about 1.5-2.5 h. A white suspension is formed (seeding may be useful to facilitate Compound 25 crystallization; the preparation of the Compound 25 seed crystals is discussed in Example 3, above). The mixture is cooled to between about 0 to about −15° C. at a rate of about 1.5° C./hour, followed by cooling to about −20° C. at a rate of about 2.5° C./hour. After holding the temperature stable for about 2 hours the solid is filtered, washed with a cold solution (∼−20° C.) composed of heptane and TBME (7:1 (vol/vol), 1.3-1.5 wt) and dried under a stream of nitrogen. Compound 25 is obtained as a white solid (approximately 0.5-0.6 wt). The filtrate is concentrated in vacuo at about 20-30° C. and recrystallized according to the procedure just described. Thus, a second crop of Compound 25 (0.2-0.3 wt) may also be obtained.

Specific example: The following procedure describes the recrystallization of Compound 25 (1.18 Kg, referred herein as 1.0 wt). In a 22 L Rotavap glass bulb under nitrogen atmosphere, urea di-phosphoramidite Compound 25 from Step 4a (1.18 Kg, 1.0 wt) was dissolved in TBME (1.81 Kg, 1.5 wt). Insoluble particulates were removed by filtration, using TBME (0.60 Kg, 0.50 wt) as a rinse. The filtrate was transferred to an inerted 30 L jacketed glass reactor equipped with a mechanical stirrer. Heptane (15.54 Kg, 13.2 wt) was added, the resultant solution was cooled to 10.3° C. Compound 25 started to precipitate about 5 min later. Stirring was continued at 9-11° C. for about 130 min. The mixture was then cooled at a rate of about 1.5° C./hour overnight to a temperature of about −15° C. The next day cooling was continued at a rate of about 1.5° C./hour to a temperature of −17.2° C., after which the temperature was held for about 2 hours between −17.0 to −20° C. The solid that was formed was then filtered, washed with a cold solution (∼−20° C.) composed of heptane and TBME (7:1 (vol/vol), 1.56 Kg, 1.3 wt), and dried under a stream of nitrogen for about 22.5 h. Compound 25 was obtained as a white solid (0.675 Kg, 0.57 wt, Purity: 93.9% area percent (HPLC TM2 of Compound 25); Yield: 36.0% from Compound 24). The filtrate was concentrated in vacuo at 20-30° C. and recrystallized according to the procedure just described. Thus, a second crop of Compound 25 was obtained as a white solid (0.225 Kg, 0.19 wt, Purity: 92.6% area percent (HPLC TM2 of Compound 25); Yield: 11.8% from Compound 24).

Analytical Data for Compound 25: $^1$H-NMR (400 MHz, CDCl$_3$) δ: 5.90-6.01 (m, 2H), 5.30 (d, J=17 Hz, 2H), 5.16 (d, J=10 Hz, 2H), 4.79 (t, J=5 Hz, 2H), 4.06-4.26 (m, 4H), 3.66-3.79 (m, 4H), 3.54-3.66 (m, 4H), 3.33-3.47 (m, 4H), 1.18 (d, J=7 Hz, 24H). ESI-MS (M+Na)$^+$ Theoretical calculation for $C_{23}H_{48}N_4NaO_5P_2$: 545.3; actual result: 545.4

Example 5

Solid State Characterization of Crystalline Compound 25

A. Powder X-ray Diffraction

Figure 4:
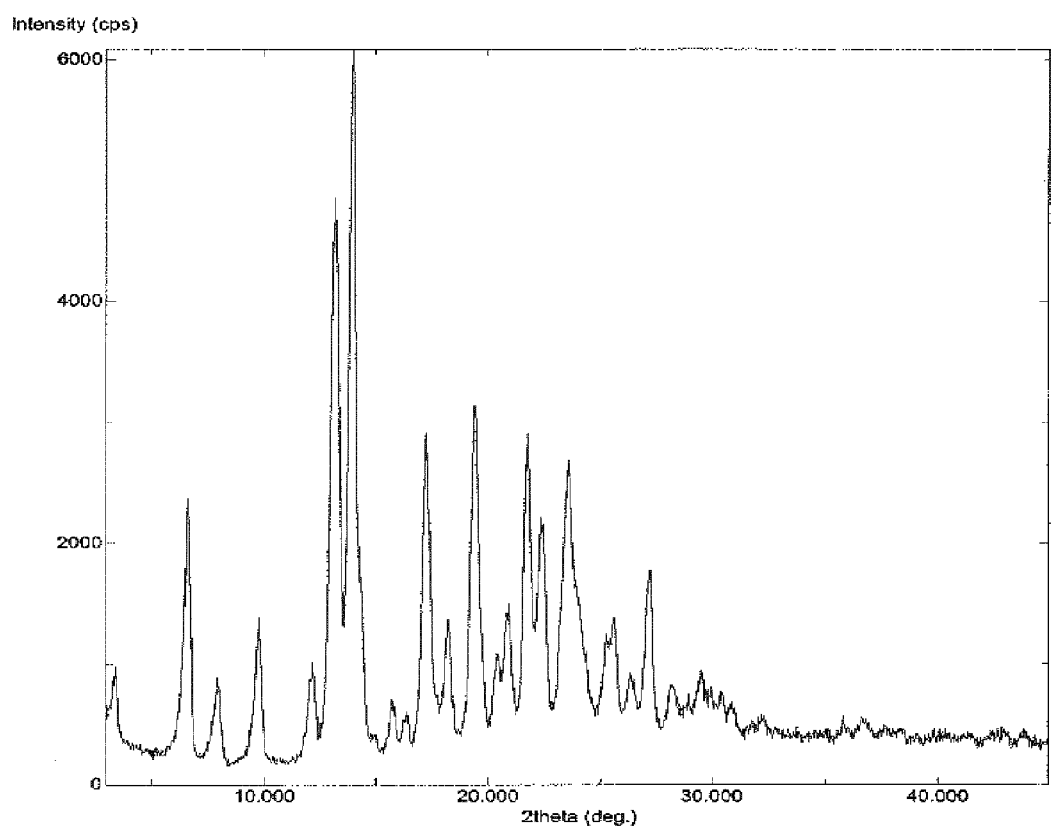
FIG. 4 is the powder X-ray diffraction pattern of crystalline Compound 25.

The powder X-ray diffraction (PXRD) pattern was obtained using the same procedure as described above in Example 2A. FIG. 4 shows the PXRD pattern of recrystallized Compound 25. The PXRD pattern shows peaks at 6.6±0.3°2Θ, 13.2±0.3°2Θ, 14.0±0.3°2Θ, 17.3±0.3°2Θ, 19.4±0.3°2Θ, 21.8±0.3°2Θ, 22.4±0.3°2Θ, 23.6±0.3°2Θ and 27.2±0.3 °2Θ. Crystalline Compound 25 may be characterized by a subset of the peaks shown in FIG. 4. For example, the following peaks are characteristic of crystalline Compound 25: 6.6±0.3°2Θ, 14.0±0.3°2Θ, 17.3±0.3°2Θ, 19.4±0.3°2Θ. Other combinations of the peaks listed or shown in FIG. 2 may be also used to identify Compound 25.

B. DSC Characterization

Figure 5:
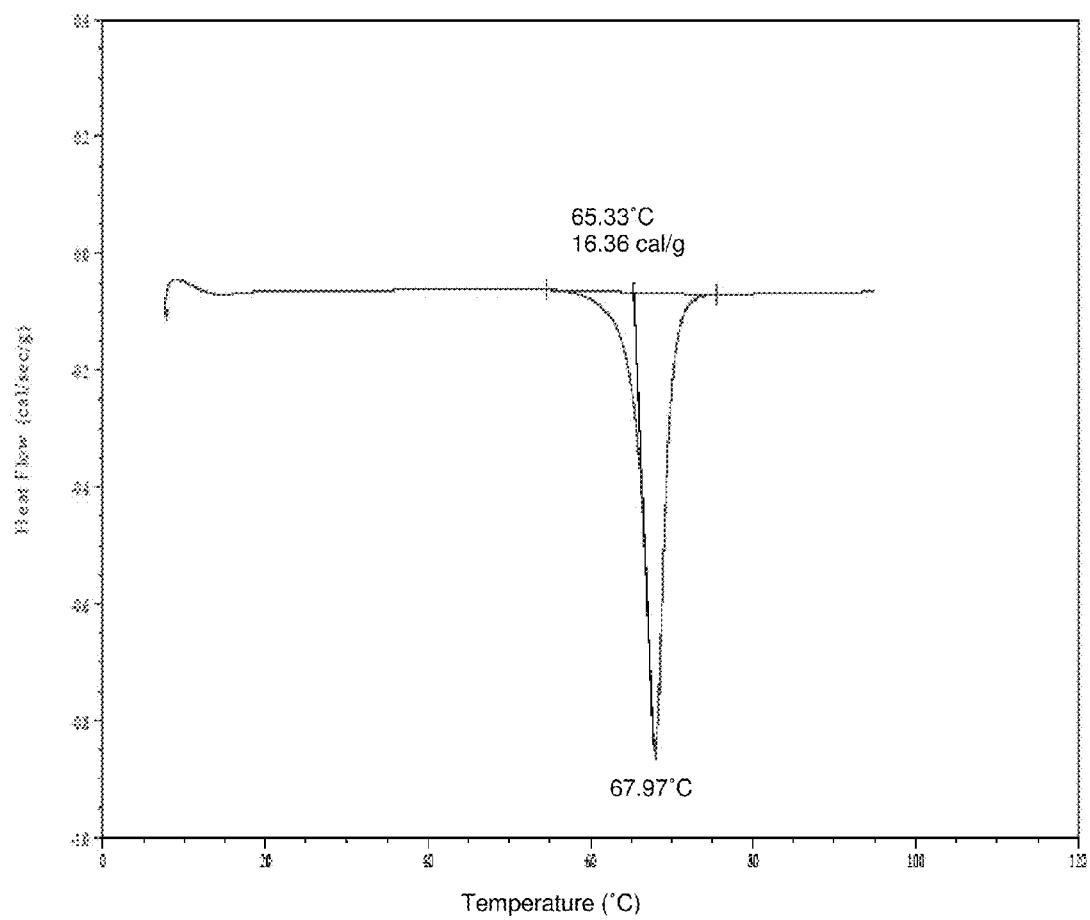
FIG. 5 is the DSC thermogram of crystalline Compound 25.

Solid-state characterization of crystalline Compound 25 was determined by Differential Scanning calorimetry (DSC, capillary technique). The DSC was run with a 2920 DSC V2.5F calorimeter heating to 100° C. at about 10° C./min under nitrogen with an aluminum pan using a 1.88 mg sample of crystalline Compound 25. FIG. 5 shows the thermograms of crystalline Compound 25, where the sample of Compound 25 melted at 65° C. (onset temp.).

A melting point experiment was also conducted using an Electrothermal Melt Temp Apparatus, with a Fluke 51 II Digital Thermometer. Compound 25 (2-3 mg) was loaded in a capillary tube (1.5-1.8×90 mm, Kimble Product KIMAX-51, part no. 34505). The observed melting point was 65-67° C.

C. Single Crystal X-ray Diffraction

Compound 25, 150 mg, was dissolved in acetonitrile, 1 mL, at about 25° C. The solution was cooled to about 0° C. over about 425 minutes and then held for about 1000 minutes. A single crystal suitable for x-ray diffraction was obtained. The crystal structure exhibited a colorless needle crystal structure having dimensions of 0.18×0.06×0.06 mm. The crystal was mounted on a 0.2 nm nylon loop using a small amount of paratone oil.

Data were collected using a Bruker SMART CCD (charge coupled device) based diffractometer equipped with an Oxford Cryostream low-temperature apparatus operating at about 193° K. Data were measured using omega scans of 0.3° per frame for about 45 seconds, such that a hemisphere was collected. A total of 1271 frames were collected with a maximum resolution of 0.76 Å. The first 50 frames were recollected at the end of data collection to monitor for decay. Cell parameters were retrieved using SMART software (SMART V 5.625 (NT) *Software for the CCD Detector System*; Bruker Analytical X-ray Systems, Madison, Wis. (2001)), and refined using SAINT on all observed reflections. Data reduction was performed using the SAINT software (SAINT V 6.22 (NT) *Software for the CCD Detector System* Bruker Analytical X-ray Systems, Madison, Wis. (2001)), which corrects for Lp and decay. Absorption corrections were applied using the SADABS multiscan technique (see SADABS, *Program for absorption corrections using Siemens CCD*, Blessing, R. H. *Acta Cryst. A*51 1995, 33-38). The structures were solved by the direct method using the SHELXS-97 program (see Sheldrick, G. M. SHELXS-90, *Program for the Solution of Crystal Structure*, University of Göttingen, Germany, 1990), and refined by the least squares method on $F^2$, SHELXL-97, (see Sheldrick, G. M. SHELXL-97, *Program for the Refinement of Crystal Structure*, University of Göttingen, Germany, 1997), incorporated in SHELXTL-PC V 6.10, (SHELXTL 6.1 (PC-Version), *Program library for Structure Solution and Molecular Graphics*; Bruker Analytical X-ray Systems, Madison, Wis., 2000). The structure showed signs of being twinned, evidenced by the initial cell parameters and peak profiles. The use of the program Cell_Now showed that there is a two fold rotation, minor twin component that is orientated along and rotated about the reciprocal axis—0.010 1.000-0.040 and real axis 0.001 1.000-0.002. The twin data was integrated and refined. The percentage of twin refinement was found to be less than 1.5%.

Figure 6:
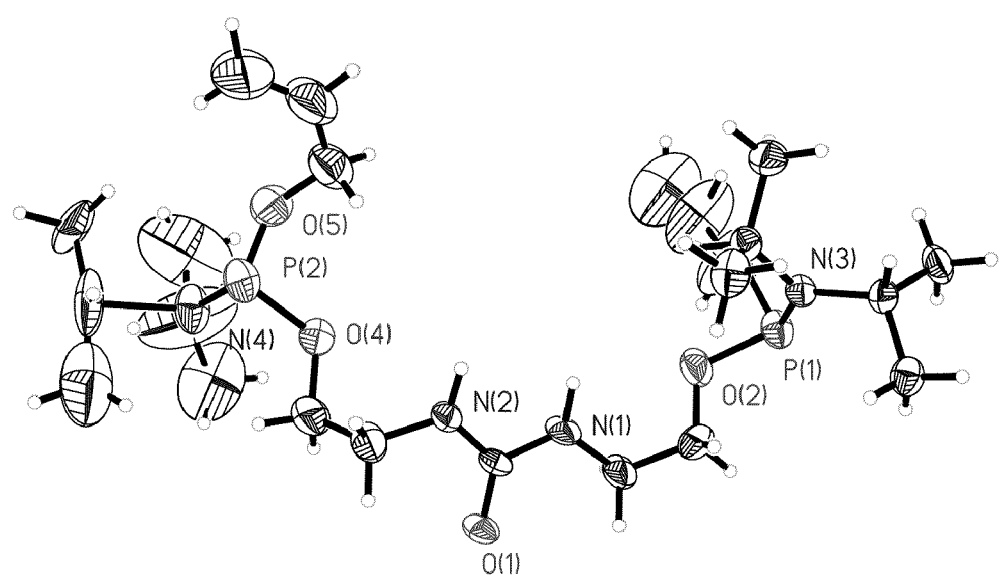
FIG. 6 is an ORTEP drawing of crystalline Compound 25 with various atomic labeling.
Figure 7:
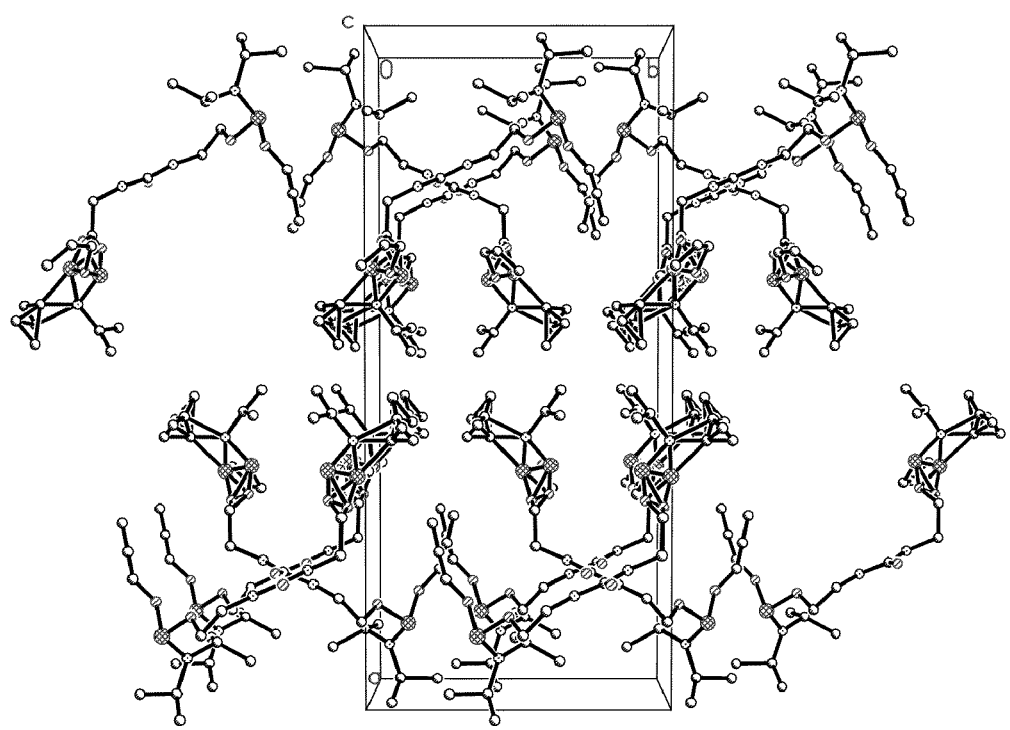
FIG. 7 is the crystal packing diagram of crystalline Compound 25 along the c-axis.

The structure was solved in the space group $P2_1/c$ (#14). All non-hydrogen atoms were refined anisotropically. Hydrogens were calculated by geometrical methods and refined as a riding model. The crystal used for the diffraction study showed no decomposition during data collection. All drawings are done at 50% ellipsoids. An ORTEP drawing of crystalline Compound 25 with various atom labeling is shown in FIG. 6. FIG. 7 shows the crystal packing diagram along the c-axis. The crystal data and structure refinement parameters are reported in Table 2.

TABLE 2

Crystal data and structure refinement for crystalline Compound 25.

| | |
|---|---|
| Empirical formula | $C_{23}H_{48}N_4O_5P_2$ |
| Formula weight | 522.59 |
| Temperature | 193(2) °K |
| Wavelength | 0.71073 Å |
| Crystal system | Monoclinic |
| Space group | P2 (1)/c |
| Unit cell dimensions | a = 27.134(14) Å  α = 90°. |
| | b = 12.135(6) Å  β = 93.156(10)°. |
| | c = 9.332(5) Å  γ = 90°. |
| Volume | 3068(3) Å$^3$ |
| Z | 4 |
| Density (calculated) | 1.131 mg/m$^3$ |
| Absorption coefficient | 0.177 mm$^{-1}$ |
| F (000) | 1136 |

TABLE 2-continued

Crystal data and structure refinement for crystalline Compound 25.

| | |
|---|---|
| Crystal size | 0.18 × 0.06 × 0.06 mm$^3$ |
| Theta range for data collection | 1.50 to 22.60° |
| Index ranges | $-22 \leq h \leq 29, -13 \leq k \leq 13,$ |
| | $-8 \leq l \leq 10$ |
| Reflections collected | 11908 |
| Independent reflections | 4010 [R (int) = 0.1578] |
| Completeness to theta = 22.60° | 99.0% |
| Absorption correction | Multiscan |
| Max. and min. transmission | 0.9895 and 0.9689 |
| Refinement method | Full-matrix least-squares on $F^2$ |
| Data/restraints/parameters | 4010/179/339 |
| Goodness-of-fit on $F^2$ | 0.970 |
| Final R indices [I > 2σ (I)] | R1 = 0.1031, wR2 = 0.2584 |
| R indices (all data) | R1 = 0.1851, wR2 = 0.3034 |
| Largest diff. peak and hole | 0.347 and -0.233 e · Å$^{-3}$ |

Figure 8:
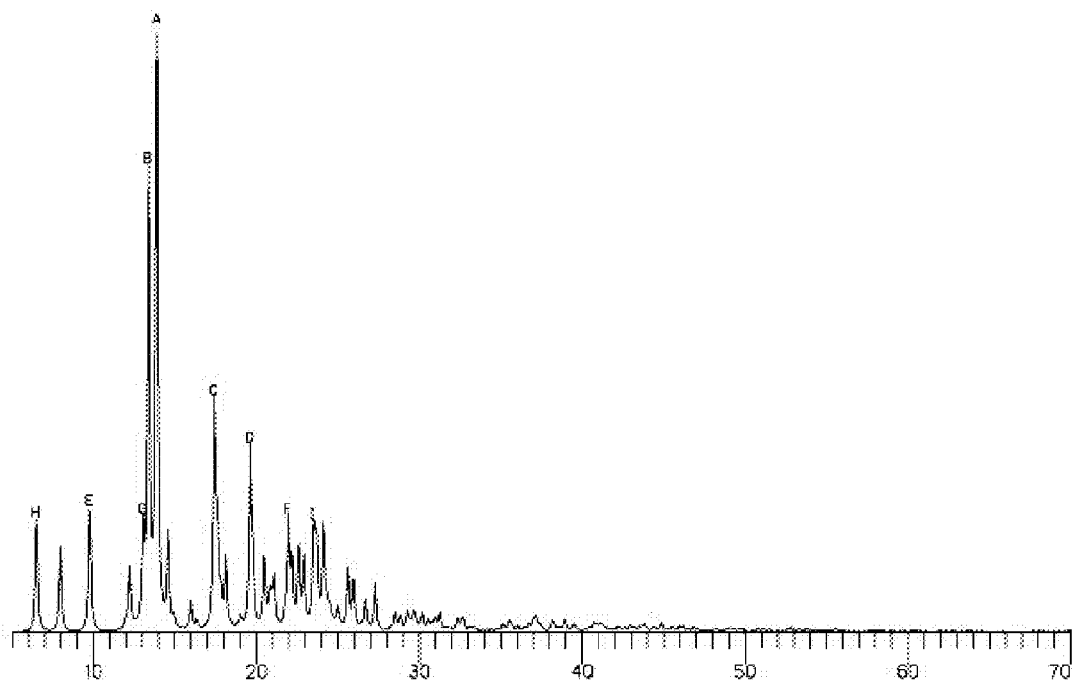
FIG. 8 is a simulated powder X-ray diffraction pattern for crystalline Compound 25.

A simulated XRPD pattern based on the single crystal data for Compound 25 is shown in FIG. 8. The powder diffraction data was simulated from the single crystal intensity data observed using the program XPOW. (XPOW, Simulated Powder Diffraction Pattern, Version 5.101, Bruker-AXS, 1997-1998.) Key parameters for the calculation include the wavelength, used copper wavelength of 1.54 Å, and the cell parameters retrieved from the final refinements. The line width and intensity is dependant on the equation:

Height=intensity/[1+4*x*x(w=v* tan (θ))]

$x=2\theta/2\theta_0$ where $2\theta_0$ is the Bragg angle for the reflection. The variables w and v are lineshape parameters. For these calculations 0.02 was used for both w and v. The table below lists the nine peaks with the highest intensity.

| Peak | Position, °2Θ |
|---|---|
| A | 13.9 |
| B | 13.4 |
| C | 17.4 |
| D | 19.6 |
| E | 9.8 |
| F | 22.0 |
| G | 13.1 |
| H | 6.5 |
| I | 23.5 |

Example 6

Preparation of Compound 26

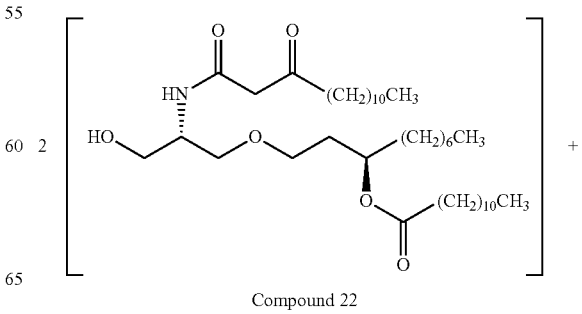

Compound 22

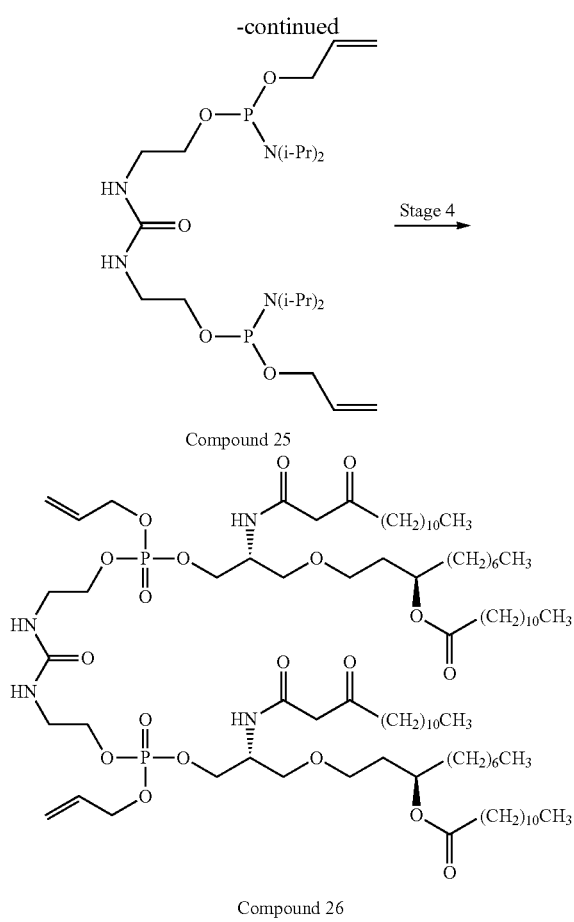

Compound 26

Stage 4: ACN, Heptane, HOAc, H₂O₂, Na₂S₂O₃, chromatography.

Preparation of Compound 26 (Step 5a)

General Procedure for the synthesis of Compound 26: (Note: 1.0 wt herein refers to the mass of Compound 22 used as starting material to produce a batch of Compound 26). In an appropriately sized and inerted glass reactor equipped with a stirring device are charged Compound 22, for example Compound 22 obtained from Steps 2b-2c, preferably Step 2c, (1.0 wt, 1.0 eq) and Compound 25, for example Compound 25 obtained from any of Steps 4a-4-b, preferably Step 4b, (0.42 wt, 0.52 eq). Anhydrous acetonitrile (5.0 wt) and anhydrous heptane (1.4 wt) are added and stiffing is initiated. The mixture is warmed to about 20-25° C. in order to dissolve all solids. Acetic acid (0.12 wt, 1.3 eq) is slowly added, maintaining the temperature at about 20-25° C. The reaction is stirred at about 20-25° C. for several hours until complete. Anhydrous heptane (8.0 wt) is charged in the reactor and the temperature is cooled to about 0-5° C. H₂O₂ 30% (wt/wt) in water (0.17 wt, 1.1 eq) is slowly added over about 0.5 h, maintaining the temperature at ≦5° C. The reaction is stirred at ≦5° C. until complete. The reaction is then cooled to about 0° C. and residual peroxides are quenched by the addition of an aqueous solution of sodium thiosulfate pentahydrate (1/1 (w/w), 0.26 wt, 0.34 eq). Stirring is continued at about 0-4° C. until the heptane layer returns a negative test for peroxides. The temperature is raised to room temperature and then the salts are filtered off and rinsed with heptane (2.3 wt). The resultant filtrate is charged into a new glass reactor and layers are allowed to separate for about 15 min. Three layers are formed, with the bottom two layers (aqueous and acetonitrile) being drained and discarded. The top, heptane layer is washed twice with acetonitrile (1.8 wt) and concentrated to dryness at about 18-25° C. Crude Compound 26 (1.2-1.5 wt) is obtained as a thick, slightly amber oil.

Specific example: The following procedure describes the preparation of Compound 26 on a scale that involved 0.565 Kg of Compound 22 with a purity of 99.4%. (The term "1.0 wt" in this example refers to 0.56 Kg, which was the actual mass of Compound 22 used as starting material to produce Compound 26.) In a 30 L inerted jacketed glass reactor equipped with a mechanical stirrer were charged Compound 22 from Step 2c (0.56 Kg (=0.565×0.994), 1.0 wt, 1.0 eq) and Compound 25 from Step 4b (0.248 Kg, Purity: 93.9%, 0.42 wt, 0.52 eq). Anhydrous acetonitrile (2.8 Kg, 5.0 wt) and anhydrous heptane (0.79 Kg, 1.4 wt) were added and stirring was initiated. The mixture was stirred and warmed to about 20-22° C. in order to dissolve all solids. Acetic acid (0.068 Kg, 0.12 wt, 1.3 eq) was added over about 5 min while the temperature was maintained at about 22-24° C. The reaction was stirred at about 20-24° C. for about 24 h, and completion was verified by HPLC. Anhydrous heptane (4.49 Kg, 8.0 wt)) was charged into the reactor and the temperature was cooled to about 0-5° C. H₂O₂ 30% (wt/wt) in water (0.106 Kg, 0.19 wt, 1.1 eq) was slowly added over about 26 min and the temperature remained between 0-2° C. The reaction was stirred for about 3.5 h while the temperature was maintained between −1 to 2° C. The oxidation completion was confirmed by HPLC. Residual peroxides were quenched at about 0° C. by the addition of an aqueous solution of sodium thiosulfate pentahydrate (1/1 (wt/wt), 0.146 kg, 0.26 wt, 0.34 eq). Stirring was continued overnight (17.25 h) at about 0-2° C. The heptane layer was tested for the presence of peroxides (EM Quant peroxides test, EM Science, Gibbstown, N.J.), returning a negative result. The temperature was raised to about 20° C. Salts were filtered off and rinsed with heptane (1.26 Kg, 2.25 wt). The resultant filtrate was charged into a new glass reactor and layers were allowed to separate for about 15 min. Three layers were formed, and the bottom two layers (aqueous and acetonitrile) were drained and discarded. The top, heptane layer was washed twice with acetonitrile (1.0 Kg, 1.8 wt) and concentrated to dryness in vacuo at about 18-23° C. Crude Compound 26 (0.79 Kg, <1.4 wt; Purity 91.1% area percent) was obtained as a thick oil, slightly amber, containing 5.6% of residual heptane. HPLC conditions for analysis of Compound 26 (HPLC TM3 of Compound 26):

| | | |
|---|---|---|
| HPLC column | Waters Symmetry 300 ™ C18, 250 × 4.6 mm 5 µm | |
| Temperature | 55° C. | |
| Flow rate | 1.0 mL/min | |
| Mobile Phase A | 20 mL 85% phosphoric acid in 1000 mL water | |
| Mobile Phase B | 20 mL 85% phosphoric acid in 1000 mL ethanol | |
| | time, min | %-Solvent B |
| Gradient | initial | 30 |
| | 15 | 92 |
| | 35 | 92 |
| | 45 | 100 |
| | 60 | 100 |
| Injection Volume | 20 µL | |
| Detection | UV = 215 nm | |
| Compound 26 Retention Time | 33.1 min ± 10% | |

Compound 26 Purification (Step 5b)

General Procedure for the purification of Compound 26: (Note: 1.0 wt herein refers to the amount of Compound 22 used to produce crude Compound 26). Crude Compound 26, e.g., as obtained from the Step 5a (approximately 1.2-1.5 wt) is dissolved in a mixture of isopropanol and ethyl acetate (1/99 (vol/vol), 2 wt) and the resultant solution is loaded onto a Biotage silica gel column (approximately 10 wt of $SiO_2$) pre-equilibrated with a mixture of isopropanol and ethyl acetate (1/99 (vol/vol), approximately 55 wt). Separation is performed using isopropanol/ethyl acetate (3/97 (vol/vol), approximately 80 wt) followed by isopropanol/ethyl acetate (10/90 (vol/vol), approximately 110 wt). Preferably, around thirty-five fractions of ~4 wt are collected, including, e.g., fractions containing ≧1% of the theoretical yield of Compound 26 (≧0.0127 wt of Compound 26, (HPLC assessment)). Desired fractions are combined and concentrated in vacuo at about 20-30° C. to yield a clear oil. The clear oil is dissolved in heptane (approximately 7.0 wt) and the resultant solution is concentrated to dryness in vacuo at about 20-30° C. The heptane treatment is repeated once again and Compound 26 (1.0-1.15 wt; Yield: 75-85%) is obtained as a colorless clear oil.

Specific Example: Purification of crude Compound 26 (0.79 Kg). Note: 1.0 wt herein refers to the amount of Compound 22 (0.56 Kg) used to produce crude Compound 26. Crude Compound 26 from Step 5a (0.79 Kg, <1.4 wt) was dissolved in a mixture of isopropanol and ethyl acetate (1/99 (vol/vol), 1.18 Kg, 2.1 wt) and the resultant solution was loaded onto a Biotage KP-Sil 150L (5.0 Kg of silica, 8.9 wt.) column pre-equilibrated with a mixture of isopropanol and ethyl acetate (1/99 (vol/vol), 31.5 Kg, 56.3 wt). The column was run with isopropanol/ethyl acetate (3/97 (vol/vol), 43.9 Kg, 78.4 wt) followed by isopropanol/ethyl acetate (10/90 (vol/vol), 62.3 Kg, 111.3 wt). Thirty-six fractions of approximately 2.3 kg (approximately 4.1 wt) each were collected. Fractions containing ≧1% of the theoretical yield of Compound 26 (≧7.1 g of Compound 26), in this case fractions 7 to 31, were combined and concentrated in vacuo at 21-28° C. to a clear oil. The clear oil was dissolved in heptane (3.9 Kg, 7.0 wt) and the resultant solution was concentrated to dryness in vacuo at 24-30° C. The heptane treatment was repeated once again and Compound 26 (0.60 kg, 1.07 wt; Purity: 93.4% (HPLC TM3 of Compound 26); Yield=78.8%) was obtained as a colorless clear oil.

Analytical Data for Compound 26: $^1$H-NMR (400 MHz, $CDCl_3$) δ: 7.4-7.57 (m, 2H), 6.06 (t, J=5 Hz, 2H), 5.84-6.04 (m, 2H), 5.36 (d, J=17 Hz, 2H), 5.25 (d, J=10 Hz, 2H), 5.02 (m, 2H), 4.54 (m, 4H), 4.24 (m, 2H), 3.96-4.20 (m, 8H), 3.38-3.55 (m, 16H), 2.52 (t, J=7 Hz, 4H), 2.28 (t, J=7 Hz, 4H), 1.68-1.91 (m, 4H), 1.47-1.67 (m, 12H), 1.18-1.37 (m, 84H), 0.89 (t, J=7 Hz, 18H). ESI-MS (M+Na)$^+$ Theoretical calculation for $C_{89}H_{168}N_4NaO_{19}P_2$: 1682.2; actual result: 1682.3.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the spirit and scope of the present invention. All such modifications are intended to be within the scope of the claims appended hereto.

All patents and publications cited above are hereby incorporated by reference.

The claimed invention is:

1. A compound of formula (3):

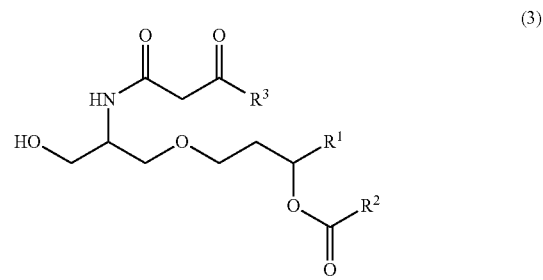

wherein:
$R^1$ is a $C_5$-$C_{15}$ alkyl group, a $C_5$-$C_{15}$ alkenyl group, or a $C_5$-$C_{15}$ alkynyl group;
$R^2$ is a $C_5$-$C_{15}$ alkyl group, a $C_5$-$C_{15}$ alkenyl group, or a $C_5$-$C_{15}$ alkynyl group; and
$R^3$ is a $C_5$-$C_{15}$ alkyl group, a $C_5$-$C_{15}$ alkenyl group, or a $C_5$-$C_{15}$ alkynyl group.

2. A compound according to claim 1, wherein
$R^1$ is a $C_5$-$C_{12}$ alkyl group,
$R^2$ is a $C_7$-$C_{14}$ alkyl group, and
$R^3$ is a $C_7$-$C_{14}$ alkyl group.

3. A compound according to claim 2, wherein
$R^1$ is a $C_7$ alkyl group,
$R^2$ is a $C_{11}$ alkyl group, and
$R^3$ is a $C_{11}$ alkyl group.

4. A compound according to claim 3, wherein
$R^1$ is an n-heptyl group,
$R^2$ is an n-undecyl group, and
$R^3$ is an n-undecyl group.

5. A compound according to claim 1, where at least one of $R^1$, $R^2$ and $R^3$ is different from the others.

6. A compound according to claim 1, having the stereochemistry of formula (3a):

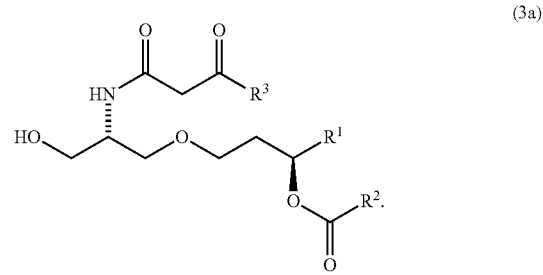

7. A compound according to claim 6, wherein the compound is compound 22:

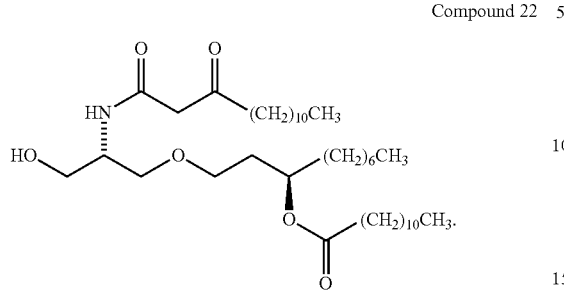

Compound 22

8. A process for making a compound of formula (3) by a reaction of a compound of formula (1) with a compound of formula (2) as shown below

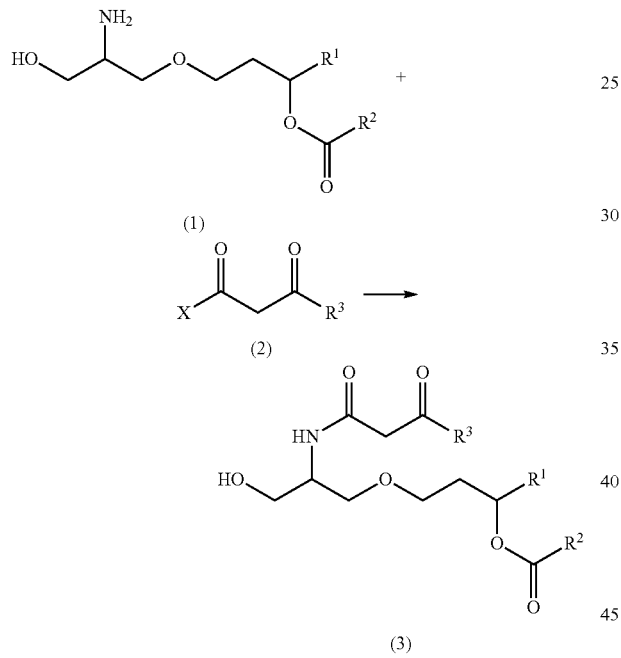

wherein:
$R^1$ is a $C_5$-$C_{15}$ alkyl group, a $C_5$-$C_{15}$ alkenyl group, or a $C_5$-$C_{15}$ alkynyl group;
$R^2$ is a $C_5$-$C_{15}$ alkyl group, a $C_5$-$C_{15}$ alkenyl group, or a $C_5$-$C_{15}$ alkynyl group;
$R^3$ is a $C_5$-$C_{15}$ alkyl group, a $C_5$-$C_{15}$ alkenyl group, or a $C_5$-$C_{15}$ alkynyl group; and
X is a leaving group.

9. A process according to claim 8, wherein
$R^1$ is a $C_5$-$C_{12}$ alkyl group,
$R^2$ is a $C_7$-$C_{14}$ alkyl group,
$R^3$ is a $C_7$-$C_{14}$ alkyl group, and X is OH, Cl, F, imidazolidyl, trimethyl acetoxy, ethyl carbonate, methyl carbonate, isobutyl carbonate, or a group of the formula Z:

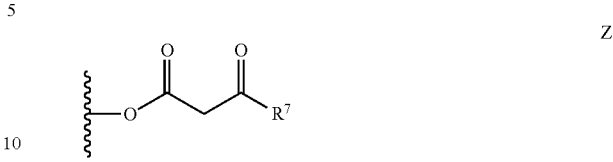

Z wherein $R^7$ and $R^3$ in formula (2) are identical such that the compound of formula (2) is a symmetrical beta ketoester anhydride.

10. A process according to claim 9, wherein
$R^1$ is a $C_7$ alkyl group;
$R^2$ is a $C_{11}$ alkyl group; and
$R^3$ is a $C_{11}$ alkyl group.

11. A process according to claim 10, wherein
$R^1$ is an n-heptyl group;
$R^2$ is an n-undecyl group; and
$R^3$ is an n-undecyl group.

12. A process according to claim 8, where at least one of $R^1$, $R^2$ and $R^3$ is different from the others.

13. A process according to claim 8, further comprising the step of hydrogenating a compound of formula Y:

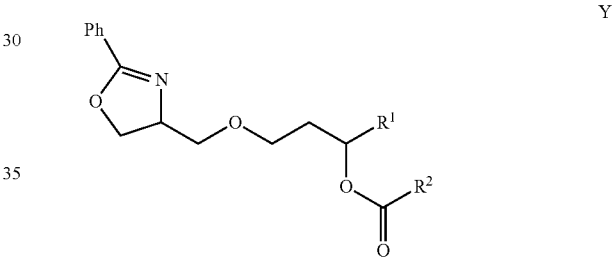

Y in isopropanol to form a compound of formula (1).

14. Crystalline compound 22

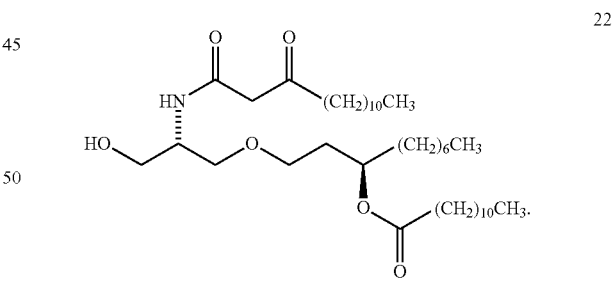

22 characterized by an x-ray powder diffraction pattern having peaks at 12.3±0.2°Θ, 14.5 ±0.2°Θ, 16.2±0.2°Θ, 17.8±0.2°Θ, 22.2±0.2°Θ, and 23.8±0.2°Θ.

15. Crystalline compound 22 according to claim 14, further characterized by having a melting point of about 41° C.

* * * * *